US012800577B2

(12) United States Patent
Mcintosh et al.

(10) Patent No.: US 12,800,577 B2
(45) Date of Patent: Nov. 17, 2026

(54) SENSOR DEVICE FOR ELECTROCHEMICAL ANALYSIS OF BIOLOGICAL SAMPLES

(71) Applicant: Foothold Labs Inc., Olathe, KS (US)

(72) Inventors: Sean Mcintosh, Lawrence, KS (US); Joshua Sestak, North Liberty, IA (US)

(73) Assignee: FOOTHOLD LABS INC., Olathe, KS (US)

( * ) Notice: Subject to any disclaimer, the term of this patent is extended or adjusted under 35 U.S.C. 154(b) by 793 days.

(21) Appl. No.: 18/087,304

(22) Filed: Dec. 22, 2022

(65) Prior Publication Data

US 2023/0204570 A1 Jun. 29, 2023

Related U.S. Application Data

(60) Provisional application No. 63/293,509, filed on Dec. 23, 2021.

(51) Int. Cl.
*G01N 33/543* (2006.01)
*G01N 27/30* (2006.01)
*G01N 27/327* (2006.01)

(52) U.S. Cl.
CPC ....... *G01N 33/5438* (2013.01); *G01N 27/308* (2013.01); *G01N 27/3275* (2013.01); *G01N 33/54353* (2013.01)

(58) Field of Classification Search
CPC ............. G01N 33/5438; G01N 27/308; G01N 27/3275; G01N 33/54353; G01N 27/3277
See application file for complete search history.

(56) References Cited

U.S. PATENT DOCUMENTS 4,715,237 A 12/1987 Kaempf et al.
5,062,547 A 11/1991 Zahner et al.
(Continued)

FOREIGN PATENT DOCUMENTS

CN 106732835 A 5/2017
EP 2381250 A1 10/2011
(Continued)

OTHER PUBLICATIONS

Malvano et al., “A new label-free impedimetric aptasensor for gluten detection,” 2017, Food Control, vol. 79, pp. 200-206 (Year: 2017).*

(Continued)

*Primary Examiner* — Shizhi Qian
(74) *Attorney, Agent, or Firm* — Wilson Sonsini Goodrich & Rosati

(57) ABSTRACT

Systems, devices, and methods are described herein for using a biosensor to detect a target species in a biological sample by electrochemical methods. The systems include a biosensor comprising a working electrode, an anchor layer, a linker, and a recognition component. Optionally, the biosensor can also include a visualization component for characterization of the biosensor by one or more microscopy techniques. In some embodiments, the methods disclosed herein include mixing a reporter molecule with a biological sample to produce a mixture, flowing the resulting mixture over the biosensor, applying an excitation signal to the electrode to initiate a chemical reaction between the reporter molecule, the target species, and the biosensor, sensing a response signal from the biosensor in response to the excitation signal, and determining, based on the response to the excitation signal, the concentration of the target species present in the sample.

18 Claims, 17 Drawing Sheets

(56) References Cited

U.S. PATENT DOCUMENTS

| | | | |
|---|---|---|---|
| 5,110,429 | A | 5/1992 | Novotny et al. |
| 5,296,193 | A | 3/1994 | Reger et al. |
| 5,512,131 | A | 4/1996 | Kumar et al. |
| 5,686,829 | A | 11/1997 | Girault |
| 5,861,097 | A | 1/1999 | Schafer et al. |
| 6,153,101 | A | 11/2000 | Schafer et al. |
| 6,182,517 | B1 | 2/2001 | Zahner |
| 7,019,040 | B2 | 3/2006 | Seubert et al. |
| 7,288,394 | B2 | 10/2007 | Ostuni et al. |
| 7,753,238 | B2 | 7/2010 | Kirschenbuhler et al. |
| 7,767,146 | B2 | 8/2010 | Kirschenbuhler |
| 7,863,053 | B2 | 1/2011 | Lyng et al. |
| 8,809,065 | B2 | 8/2014 | Mutharasan et al. |
| 8,973,447 | B2 | 3/2015 | Volckens et al. |
| 9,618,439 | B2 | 4/2017 | Volckens et al. |
| 9,618,474 | B2 | 4/2017 | Van et al. |
| 9,618,476 | B2 | 4/2017 | Goldsmith |
| 9,765,395 | B2 | 9/2017 | Goldsmith |
| 9,857,328 | B2 | 1/2018 | Hoffman |
| 9,859,394 | B2 | 1/2018 | Hoffman et al. |
| 10,006,910 | B2 | 6/2018 | Hoffman |
| 10,020,300 | B2 | 7/2018 | Hoffman |
| 10,119,968 | B2 | 11/2018 | Lansing |
| 10,139,270 | B2 | 11/2018 | Mutharasan et al. |
| 10,395,928 | B2 | 8/2019 | Pan et al. |
| 10,413,621 | B2 | 9/2019 | Basilion et al. |
| 10,429,342 | B2 | 10/2019 | Hoffman et al. |
| 10,429,381 | B2 | 10/2019 | Hoffman |
| 10,494,670 | B2 | 12/2019 | Van Rooyen et al. |
| 10,607,989 | B2 | 3/2020 | Hoffman |
| 10,737,855 | B2 | 8/2020 | Christensen et al. |
| 10,751,986 | B2 | 8/2020 | Lerner et al. |
| 10,759,157 | B2 | 9/2020 | Lerner et al. |
| 10,811,539 | B2 | 10/2020 | Van Rooyen et al. |
| 10,875,339 | B1 | 12/2020 | Claussen et al. |
| 10,876,210 | B1 | 12/2020 | Claussen et al. |
| 10,903,319 | B2 | 1/2021 | Pan et al. |
| 10,968,481 | B2 | 4/2021 | Van Rooyen et al. |
| 11,717,202 | B2 | 8/2023 | Mcintosh |
| 2002/0027085 | A1 | 3/2002 | Stori et al. |
| 2003/0190259 | A1 | 10/2003 | Alley |
| 2004/0082749 | A1 | 4/2004 | Seubert et al. |
| 2004/0171135 | A1 | 9/2004 | Ostuni et al. |
| 2004/0253150 | A1 | 12/2004 | Kirschenbuhler |
| 2006/0003382 | A1 | 1/2006 | Eckermann et al. |
| 2006/0045805 | A1 | 3/2006 | Kirschenbuhler |
| 2007/0194055 | A1 | 8/2007 | Kirschenbuhler et al. |
| 2008/0145908 | A1 | 6/2008 | Ostuni et al. |
| 2009/0065357 | A1 | 3/2009 | Glezer et al. |
| 2009/0081785 | A1 | 3/2009 | Ho et al. |
| 2009/0090022 | A1 | 4/2009 | Ho et al. |
| 2009/0118382 | A1 | 5/2009 | Raskop et al. |
| 2009/0197283 | A1 | 8/2009 | Gold et al. |
| 2010/0297687 | A1 | 11/2010 | Mutharasan et al. |
| 2011/0027861 | A1 | 2/2011 | Ho et al. |
| 2011/0097795 | A1 | 4/2011 | Ho et al. |
| 2011/0171754 | A1 | 7/2011 | Redmond et al. |
| 2012/0082977 | A1 | 4/2012 | Rajagopal et al. |
| 2012/0207684 | A1 | 8/2012 | Basilion et al. |
| 2012/0238008 | A1 | 9/2012 | Henry et al. |
| 2012/0244606 | A1 | 9/2012 | Takeshita |
| 2012/0269730 | A1 | 10/2012 | Mirkin et al. |
| 2012/0302456 | A1 | 11/2012 | Whitesides et al. |
| 2013/0059380 | A1 | 3/2013 | Ho et al. |
| 2013/0133441 | A1 | 5/2013 | Volckens et al. |
| 2013/0205902 | A1 | 8/2013 | Mutharasan et al. |
| 2014/0120520 | A1 | 5/2014 | Ho et al. |
| 2014/0360890 | A1 | 12/2014 | Mutharasan et al. |
| 2015/0064723 | A1 | 3/2015 | Mutharasan et al. |
| 2015/0143929 | A1 | 5/2015 | Volckens et al. |
| 2015/0157009 | A1 | 6/2015 | Ho et al. |
| 2015/0253296 | A1 | 9/2015 | Christensen et al. |
| 2015/0307936 | A1 | 10/2015 | Goldsmith |
| 2015/0309018 | A1 | 10/2015 | Goldsmith |
| 2016/0025675 | A1 | 1/2016 | Goldsmith |
| 2016/0052683 | A1 | 2/2016 | Christensen et al. |
| 2016/0054312 | A1 | 2/2016 | Goldsmith |
| 2016/0178569 | A1 | 6/2016 | Hoffman et al. |
| 2016/0265047 | A1 | 9/2016 | Van Rooyen et al. |
| 2017/0018626 | A1 | 1/2017 | Hoffman et al. |
| 2017/0053908 | A1 | 2/2017 | Hoffman |
| 2017/0059514 | A1 | 3/2017 | Hoffman |
| 2017/0102358 | A1 | 4/2017 | Hoffman |
| 2017/0218442 | A1 | 8/2017 | Van Rooyen et al. |
| 2017/0307562 | A1 | 10/2017 | Goldsmith |
| 2017/0361599 | A1 | 12/2017 | Lerner et al. |
| 2017/0365474 | A1 | 12/2017 | Pan et al. |
| 2017/0365477 | A1 | 12/2017 | Pan et al. |
| 2017/0365562 | A1 | 12/2017 | Pan et al. |
| 2018/0037952 | A1 | 2/2018 | Goldsmith |
| 2018/0311664 | A1 | 11/2018 | Lansing et al. |
| 2018/0315750 | A1 | 11/2018 | Hoffman |
| 2018/0339292 | A1 | 11/2018 | Katz et al. |
| 2019/0120830 | A1 | 4/2019 | Hoffman |
| 2019/0125316 | A1 | 5/2019 | Tariyal et al. |
| 2019/0181273 | A1 | 6/2019 | Van Rooyen et al. |
| 2019/0262827 | A1 | 8/2019 | Lalonde et al. |
| 2019/0271693 | A1* | 9/2019 | Lakshmana .............. C12Q 1/68 |
| 2019/0351665 | A1 | 11/2019 | Lerner et al. |
| 2020/0009271 | A1 | 1/2020 | Basilion et al. |
| 2020/0025753 | A1 | 1/2020 | Claussen et al. |
| 2020/0038866 | A1 | 2/2020 | Henry et al. |
| 2020/0141931 | A1 | 5/2020 | Hoffman |
| 2020/0181695 | A1 | 6/2020 | Van Rooyen et al. |
| 2020/0215488 | A1 | 7/2020 | Laubli et al. |
| 2020/0323474 | A1 | 10/2020 | Mcintosh |
| 2020/0339322 | A1 | 10/2020 | Christensen et al. |
| 2024/0156380 | A1 | 5/2024 | Mcintosh |

FOREIGN PATENT DOCUMENTS

| | | | |
|---|---|---|---|
| JP | 2013253962 | A | 12/2013 |
| WO | WO-2021207693 | A1 | 10/2021 |

OTHER PUBLICATIONS

Srisombat et al., "Stability: A key issue for self-assembled monolayers on gold as thin-film coatings and nanoparticle protectants," 2011, Colloids and Surfaces A: Physicochemical and Engineering Aspects, vol. 390, pp. 1-19 (Year: 2011).*

Liu et al., "Square wave voltammetry versus electrochemical impedance spectroscopy as a rapid detection technique at electrochemical immunosensors," 2010, Biosensors and Bioelectronics, vol. 25, pp. 1467-1473 (Year: 2010).*

Alsefri et al., Electrochemical development of an immunosensor for detection of polychlorinated biphenyls (PCBs) for environmental analysis, Chemosensors, 2021, 9, 307 (Year: 2021).*

Welch et al., Orientation and characterization of immobilized antibodies for improved immunoassays (Review), Biointer Phases, 2017, 12(2), 02D301 (Year: 2017).*

European Patent Office, International Search Report and Written Opinion for PCT/US2021/026708, Jul. 22, 2021, 20 pages.

The International Bureau of WIPO, International Preliminary Report on Patentability for PCT/US2021/026708, Oct. 20, 2022, 13 pages.

Cooper, Christopher D. et al.: Probing protein orientation near charged nanosurfaces for simulation-assisted biosensor design, Journal of Chemical Physics 143, 124709 (2015), doi:10.1063/1.4931113.

Gajos, Katarzyna et al.: A perspective on ToF-SIMS analysis of biosensor interfaces: Controlling and optimizing multi-molecular composition, immobilization through bioprinting, molecular orientation, Applied Surface Science 594:153439 (2022), https://doi.org/10.1016/j.apsusc.2022.153439.

Gunnarsson, Anders et al.: Regenerable Biosensors for Small-Molecule Kinetic Characterization Using SPR, SLAS Discovery: Advancing the Science of Drug Discovery 26(5) 730-739 (2021), doi:10.1177/2472555220975358.

Trilling, Anke K. et al.: Antibody orientation on biosensor surfaces: a minireview, Analyst 138:1619-1627 (2013), doi:10.1039/c2an36787d.

(56) References Cited

OTHER PUBLICATIONS

Wei, Yu-ping et al.: Highly sensitive electrochemical biosensor for streptavidin detection based on CdSe quantum dots, Biosensors and Bioelectronics 103:99-103 (2018), https://doi.org/10.1016/j.bios.2017.12.024 (abstract and introduction).

* cited by examiner

SENSOR DEVICE FOR ELECTROCHEMICAL ANALYSIS OF BIOLOGICAL SAMPLES

RELATED APPLICATIONS

This application claims priority to and the benefit of U.S. Provisional Patent Application No. 63/293,509, entitled "Sensor Device for Electrochemical Analysis of Biological Samples," filed Dec. 23, 2021, the disclosure of which is hereby incorporated by reference in its entirety.

TECHNICAL FIELD

The present disclosure relates to sensor devices for the electrochemical analysis of samples, and more particularly to electrochemical biosensors having functionalized surfaces configured to quantify target species present at low concentrations in biological samples.

BACKGROUND

The analysis of samples to detect, monitor and/or quantify species present in low concentrations has gained significant interest due to a wide range of potential applications including detection of trace quantities of explosives, narcotics, toxic industrial chemicals, as well as detection and quantification of key biomarkers such as proteins, small molecules, and nucleic acids related to disease diagnosis, personalized medicine, and point-of-care testing (POCT). Electrochemical sensor devices provide an attractive approach to analyze samples, particularly complex biological samples (e.g., electrochemical biosensors), due to their direct conversion of a chemical or biological event into an easily measurable electrical signal. Despite recent advances, the majority of electrochemical biosensors devices require use of elaborate experimental equipment, involve tedious calibration procedures best suited for centralized laboratories operated by highly trained personnel, and/or may exhibit low selectivity and sensitivity. For example, current electrochemical biosensors may require use large non-disposable electrodes that need to be stored, cleaned and calibrated frequently according to tedious and time-consuming methods in order to ensure accurate and reproducible results. These biosensor devices can be expensive, lack portability (e.g., devices designed for bench top applications) and thus are not suitable for rapid detection of biological species on field applications such as, for example by law enforcement, military, customs, airport security, POCT and others. Consequently, there is a need for biosensor devices that overcome the limitations of current technology.

SUMMARY

Apparatus, systems, and methods are described herein for the electrochemical analysis of biological samples to quantify target species present at low concentrations.

In some embodiments a biosensor configured to detect a target species comprises: an electrode configured to receive an electrical signal; an anchor layer disposed on the electrode and including a first chemical functionality and a second chemical functionality, the first chemical functionality being configured to immobilize the anchor layer to the electrode; a linker covalently bound to the second chemical functionality of the anchor layer; and a recognition component conjugated to the linker and disposed at an orientation with respect to the electrode. The recognition component is configured to selectively bind the target species when the electrical signal is received by the electrode.

In some embodiments the electrode comprises a a conductive material selected from gold, platinum, carbon, and graphene.

In some embodiments the electrode includes a screen-printed electrode.

In some embodiments the first chemical functionality of the anchor layer comprises a sulfur-containing group selected from a thiol, a disulfide, and a sulfide group.

In some embodiments the second chemical functionality of the anchor layer includes a carboxylic group.

In some embodiments the anchor layer includes 2-carboxyethyl disulfide.

In some embodiments the linker includes a biotin-binding protein.

In some embodiments the biotin-binding protein is streptavidin.

In some embodiments the recognition component is a biotinylated antibody.

In some embodiments the orientation of the recognition component is a tail-on orientation.

In some embodiments the target species includes a CAS9 recombinant protein, C-Reactive protein (CRP), Norovirus VP1 protein, and Interleukin proteins.

In some embodiments the electrical signal includes at least one of a differential pulse voltammetry signal or a square wave voltammetry signal.

In some embodiments the biosensor is configured to have picomolar sensitivity.

In some embodiments a system comprises: a sample processing unit configured to receive a biological sample suspected of having a target species; an electrochemical testing unit configured to generate an electrical signal; and a biosensor coupled to the electrochemical testing unit and configured to be disposed in the sample processing unit to be in physical contact with the biological sample.

In some embodiments, the sample processing unit includes a cartridge.

In some embodiments the sample processing unit is configured to receive a syringe.

In some embodiments the sample processing unit includes a first compartment configured to receive the biological sample, and a second compartment configured to receive a reporter molecule, wherein the first compartment is fluidically coupled to the second compartment via a microfluidic channel.

In some embodiments the electrical signal includes at least one of a differential pulse voltammetry signal or a square wave voltammetry signal.

In some embodiments, a method of detecting a target species comprises: adding a reporter molecule to a biological sample suspected of having the target species to produce a biological sample mixture; contacting the biological sample mixture with the biosensor described herein, the biosensor being coupled to an electrochemical testing unit; generating with the electrochemical testing unit, an electrical signal; applying the electrical signal to the biological sample mixture via the electrode; sensing, with the electrochemical testing unit, a response signal in response to the applied electrical signal; and determining, based on the response signal, a concentration of the target species in the biological sample.

In some embodiments the reporter molecule includes at least one of a ferrocyanide compound, a ferricyanide compound, ferrocene, and methylene blue.

In some embodiments the electrical signal includes at least one of a differential pulse voltammetry signal or a square wave voltammetry signal.

In some embodiments the electrode includes at least one of a gold, carbon, and/or graphene electrode.

In some embodiments the recognition component includes a biotinylated antibody.

In some embodiments the biological sample is a saliva sample, a urine sample, a blood sample, a plasma sample, or a serum sample.

In some embodiments the method further comprises comparing the response signal with a control signal measured with a control sample by the biosensor.

In some embodiments the concentration of the target species is determined by a difference between the response signal and the control signal.

In some embodiments, a method of fabricating a biosensor comprises: contacting a first solution comprising an anchor layer with an electrode for a first period of time, the anchor layer including a first chemical functionality and a second chemical functionality, the first chemical functionality being configured to immobilize the anchor layer to the electrode; flowing a gas stream over the electrode; contacting a second solution comprising a site-blocking reagent with the electrode for a second period of time; contacting third solution comprising a linker with the electrode for a third period of time, the linker being configured to bind to the second chemical functionality of the anchor layer; and contacting a fourth solution comprising a recognition component with the electrode for a fourth period of time, while an electrical signal is applied to the electrode.

DETAILED DESCRIPTION

Figure 1:
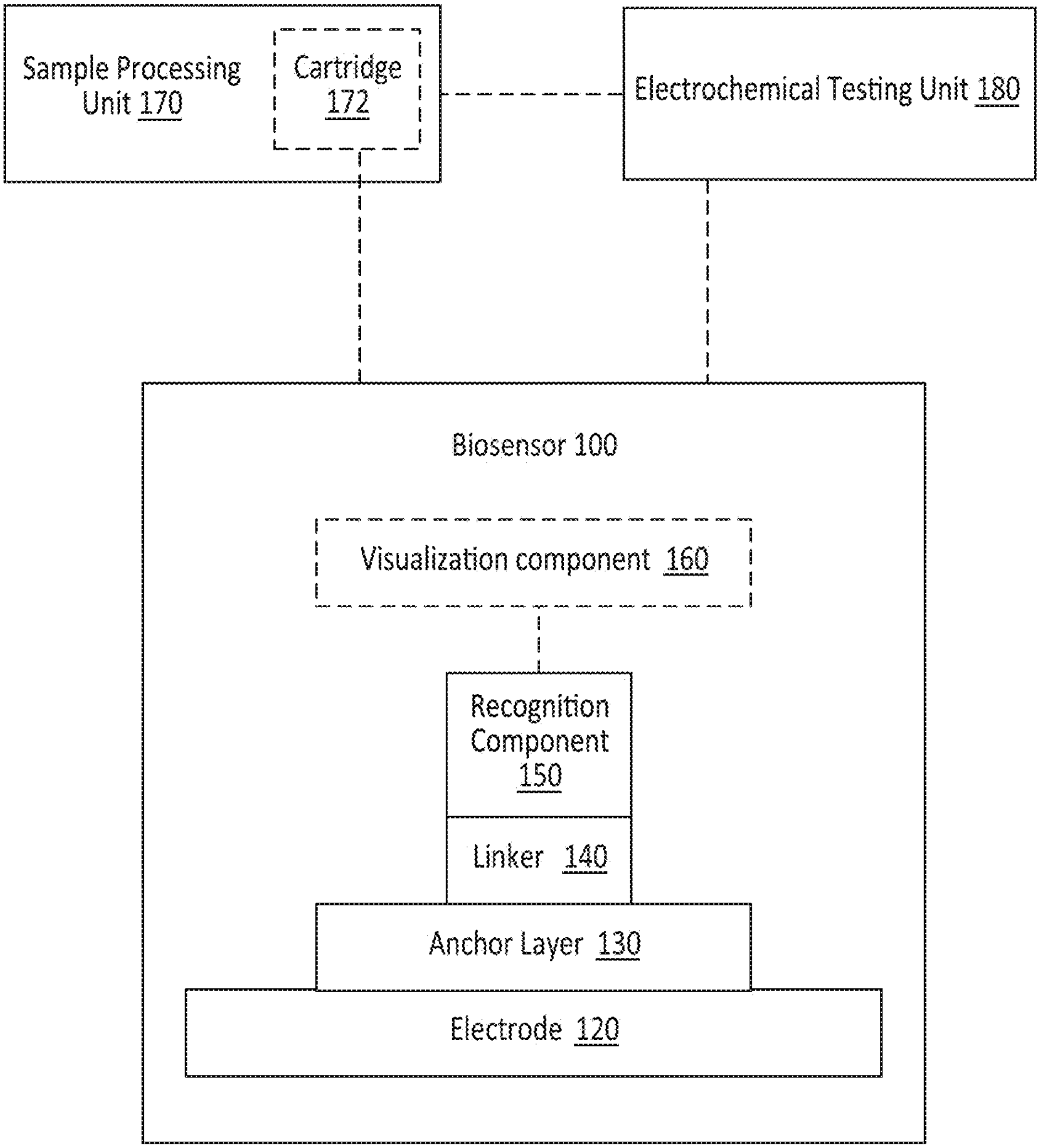
FIG. 1 is a schematic illustration of an electrochemical biosensor according to an embodiment.

The embodiments described herein relate generally to devices for the electrochemical analysis of samples, and more particularly to the fabrication and use of electrochemical biosensors that can exhibit high sensitivity and selectivity towards specific target species such as proteins, small molecules, antigens, and/or nucleic acids associated with fungi, parasites, bacteria, viruses, and/or pathogens. The electrochemical biosensors described herein enable rapid, simple, onsite, and cost-effective detection and/or monitoring of the target species as well as diagnosis of infectious diseases.

Pathogens are microorganisms such as fungi, protozoans, bacteria, and infectious agents including viruses and prions that cause disease. Common pathogens including viruses such as norovirus, and influenza virus, and bacteria such as *E coli*, can enter the body through various modes of infection (e.g., foodborne, waterborne, or airborne) and cause a wide range of illnesses and in some case death. Consequently, the development of techniques for sensitive and rapid detection of pathogens (or chemical species associated with the pathogens such as a proteins, small molecules, antigens, and/or nucleic acids) present in bodily fluids, aerosols, and on surfaces constitutes a critical step on the treatment of infectious diseases and controlling the spread of disease.

Techniques for detection and quantification of pathogens can be broadly classified as corresponding to immunoassays or DNA-based assays. Immunoassays detect pathogens through the presence of antibodies in an organism during or after the infection (e.g., after the is no longer present in organism). The antibodies or immunoglobulins (Igs) are highly soluble serum glycoproteins produced by the immune system in response to the presence of a pathogen in the organism. The antibodies act as a biorecognition component that comprises an antigen-binding fragment (Fab) configured to target a specific pathogen and bind the pathogen via non-covalent binding interactions. The detection of pathogens in immunoassays can proceed by an indirect method in which the antibody is the target molecule (e.g., the detection of the specific antibody in the organism provides an indirect evidence of the presence of the pathogen), or a direct method in which, if the antibody is available, it can be used to bind the pathogen. DNA-based assays detect pathogens through molecular biology gene amplification methods that require DNA sequence data such as viral DNA, toxin-producing genes, as well as species and strain selective genes. The use of immunoassays and/or DNA-based assays depends on multiple factors including the availability of antibodies and the availability of DNA sequence data. Common assays for the detection of pathogens include immunoassays such as the enzyme-linked immunosorbent assay (ELISA) and the DNA-based assay polymerase chain reaction (PCR). These assays have been used to detect a wide variety of pathogens, and their presence has become ubiquitous within the medical diagnostic field owing to its high specificity, reliability and adaptability. Despite these advantages, ELISA and PCR assays have limitations. For example, PCR assays involve amplification, isolation, and quantification of DNA, which are complex methods that require use of expensive instrumentation, highly specialized technical personnel, and use of a centralized laboratory. Although ELISA assays do not involve such complex methods as PCR assays, samples oftentimes require prolonged incubation times that do not permit real-time detection. Consequently, the PCR and ELISA assays do not meet the criteria for carrying out on-site rapid analysis of pathogens, limiting their use in a point-of-care testing (POCT).

Electrochemical sensor devices provide an attractive approach for analyzing samples, particularly complex biological samples, due to their direct conversion of a chemical or biological event into an easily measurable electrical signal. Electrochemical biosensors can operate by converting the chemical energy associated with binding events between target pathogens and electrode-immobilized biorecognition elements into electrical energy through a process that involves an electrode acting as transducer, and a pathogen containing electrolyte solution. Electrochemical biosensors can offer multiple advantages such as detection of pathogens using protocols that lack complex and tedious sample preparation protocols, detection of pathogens in various matrices, in situ detection of pathogens on surfaces, rapid pathogen detection using low-cost platforms, multiplexed detection of pathogens in practical matrices, and detection of pathogens via wireless actuation and data acquisition formats. Despite recent advances, the majority of currently available electrochemical molecular diagnostics devices use experimental equipment that is not portable (benchtop systems), and electrodes that lack sufficient specificity, sensitivity, and Lower Limit of Detection (LLD), which limits their applications in the fields of disease diagnosis, personalized medicine, and POCT.

The devices, systems, and methods described herein address the limitations of existing technologies by providing electrochemical biosensors comprising a biorecognition component immobilized on the surface of the electrochemical biosensor at a specific orientation which significantly improves the selectivity of the biorecognition component towards binding a target pathogen, and reduces non-specific binding events, resulting in higher specificity, higher sensitivity, and lower limits of detection when compared to other electrochemical biosensors having the same concentration of immobilized biorecognition components. In some embodiments, the electrochemical biosensors described herein can exhibit 70 to 80 times lower limits of detection when compared with conventional electrochemical biosensors having the same concentration of immobilized biorecognition components. For example, in some embodiments the electrochemical biosensors described herein can detect target species present in unfiltered and un-prepared samples that include complex matrices such as saliva, urine, blood serum, soil slurries and/or freshwater and contain interference proteins and/or chemical species, with a lower limit of detection (LLD) of at least about 5 picograms per milliliter (pg/mL, 1 pg=1×10 E-12 grams), about 10 pg/mL, about 15 pg/mL, about 20 pg/mL, about 40 pg/mL, about 60 pg/mL, about 80 pg/mL, about 100 pg/mL, about 150 pg/mL, about 200 pg/mL, about 500 pg/mL, about 750 pg/mL, about 1000 pg/mL, inclusive of all values and ranges therebetween. The specific orientation of the biorecognition component on the surface of the electrochemical biosensor stems from its fabrication process which includes sequential incorporation of multiple components configured to favor the immobilization of the biorecognition component at the specific orientation, and the of use of predetermined electric signals prior to and during conjugation of the biorecognition component to the electrochemical biosensor, as further described herein.

In some embodiments, the electrochemical biosensors described herein can be used to detect, monitor, and/or quantify the concentration of a target species that may be present in biological samples by (1) mixing the biological sample with a reporter molecule to produce a biological sample mixture, (2) exposing the biological sample mixture to the electrochemical biosensor, and (3) applying a predetermined excitation signal (e.g., an electrical signal) to the electrochemical biosensor. Without being bound by any particular theory, it is believed that the predetermined electrical signal can induce localized surface plasmon resonance on nanostructures present on the surface of the electrochemical biosensor, causing electrons to jump on the surface of the biosensor, thereby increasing their electromagnetic field and attracting and/or pulling species present in the biological sample mixture to the surface of the biosensor, thus forming an affinity cloud that improves the binding of the target species with the biorecognition component and increases significantly the sensitivity of the electrochemical biosensor. The reporter molecule can include a redox pair that can undergo a reversible electrochemical reaction that can be measured, and/or monitored via standard electrochemical methods, and that is substantially free from unwanted secondary reactions and/or processes. The reporter molecule can electrostatically oppose all the species (i.e., the target species and all non-target species) present in the biological sample mixture. The predetermined electrical signal sent to the electrochemical biosensor can cause the reporter molecule to bind with the non-target species present in the biological sample mixture and produce a strong electrical current that can be detected with the electrochemical biosensor and can be easily distinguished with machine learning software. The target species binds will not bind to the reporter molecule as the target species binds to the biorecognition component due to a much stronger affinity compared to the other non-target species. In that way, the electrical produced is inversely proportional to the concentration of target species present in the sample, as further described herein.

As used in this specification and in the claims, the singular forms "a," "an," and "the" include plural referents unless the context clearly dictates otherwise. Thus, for example, the term "a member" is intended to mean a single member or a combination of members, "a material" is intended to mean one or more materials or a combination thereof, etc.

As used herein, the terms "about," "approximately," and/or "substantially" when used in connection with a stated value(s) and/or a geometric structure(s) or relationship(s) is intended to convey that the value or characteristic so defined is nominally the value stated and/or characteristic described.

In some instances, the terms "about," "approximately," and/or "substantially" can generally mean and/or can generally contemplate a value or characteristic stated within a desirable tolerance (e.g., plus or minus 10% of the value or characteristic stated). For example, a value of about 0.01 would include 0.009 and 0.011, a value of about 0.5 would include 0.45 and 0.55, a value of about 10 would include 9 to 11, and a value of about 1000 would include 900 to 1100. While a value, structure, and/or relationship stated may be desirable, it should be understood that some variance may occur as a result of, for example, manufacturing tolerances or other practical considerations (such as, for example, the pressure or force applied through a portion of a device, conduit, lumen, etc.). Accordingly, the terms "about," "approximately," and/or "substantially" can be used herein to account for such tolerances and/or considerations.

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

As used herein, the phrase "and/or," should be understood to mean "either or both" of the elements so conjoined (e.g., elements that are conjunctively present in some cases and disjunctively present in other cases). Multiple elements listed with "and/or" should be construed in the same fashion (e.g., "one or more" of the elements so conjoined). Other elements may optionally be present other than the elements specifically identified by the "and/or" clause, whether related or unrelated to those elements specifically identified. Thus, as a non-limiting example, a reference to "A and/or B", when used in conjunction with open-ended language such as "including," "comprising," etc., can refer, in one implementation, to A only (optionally including elements other than B); in another implementation, to B only (optionally including elements other than A); and in yet another implementation, to both A and B (optionally including other elements).

As used herein, the term "or" should be understood to have the same meaning as "and/or" as defined above. For example, when separating items in a list, "or" or "and/or" shall be interpreted as being inclusive (e.g., the inclusion of at least one, but also including more than one) of a number or list of elements, and, optionally, additional unlisted items.

As used herein, the term "tail-on orientation" refers to a specific configuration that a recognition component can assume when the recognition component is bound, conjugated, attached and/or tethered to a surface of a biosensor. In the tail-on orientation, the recognition component is bound to the biosensor in such a way that a portion of the recognition component which does not comprise the sites configured to selectivity bind a target species via noncovalent binding (i.e., the tail of the recognition component) is directly attached to the surface of the biosensor, leaving another portion of the recognition component that has the sites oriented away from the surface of the biosensor. For example, in some embodiments, a recognition component can include a monoclonal antibody C-Terminus oriented according to the tail-on orientation, in which a constant fragment (Fc) of the antibody is directly attached to the surface of the biosensor or conjugated to a linker layer disposed on the surface of the biosensor, and the complementary-determining regions (CDRs) are oriented away from the surface of the biosensor and configured to be exposed to a biological sample. In some embodiments, the surface of the biosensor can be an electrode.

Referring now to the drawings, FIG. 1 is a schematic illustration of an electrochemical biosensor 100 for the detection, and quantification of target species present in biological samples according to an embodiment. The electrochemical biosensor 100, which can also be referred to as the biosensor 100, includes an electrode 120, an anchor layer 130, a linker 140, and a recognition (e.g., biorecognition) component 150. Optionally, in some embodiments, the biosensor 100 can also include a visualization component 160. The biosensor 100 can be removably coupled to a sample processing unit 170 to expose at least a portion of the biosensor 100 to biological samples stored, contained and/or housed within the sample processing unit 170. The biosensor 100 can also be removably coupled to an electrochemical testing unit 180 to conduct electrochemical analysis of biological samples suspected of comprising target species, including the biological samples stored, contained and/or housed within the sample processing unit 170. In some embodiments, the sample processing unit 170 can include a cartridge 172 configured to receive the biosensor 100, expose at least a portion of the biosensor 100 to biological samples stored on the sample processing unit 172, and couple the biosensor 100 to the electrochemical testing unit 180 to conduct electrochemical analysis of the samples stored on the sample processing unit 172, as further described herein. In some embodiments, the sample processing unit 170 and the electrochemical testing unit 180 can be similar to and/or substantially the same any of the testing receptacle and diagnostic device described in U.S. Patent Publication No. 2020/0323474, filed Apr. 10, 2020, entitled, "Mobile lab-on-a-chip diagnostic system," the disclosure of which is incorporated herein by reference in its entirety and attached hereto as Exhibit A.

The electrode 120 of the biosensor 100 can be any suitable structure that includes at least one electrically conductive surface configured to send, receive and/or exchange electrical signals which can be associated with electrochemical reactions. In some embodiments, the electrode 120 can be a multilayer component having multiple electronically conductive layers disposed and/or arranged in a suitable shape, pattern, and/or configuration such that an electrical signal can be applied to the electrode 120 to initiate, conduct and monitor electrochemical reactions. In some embodiments, the electrode 120 can be disposed on a substrate configured to provide mechanical support to the electrode 120 and other components of the biosensor 100. In some embodiments, the electrode 120 can include multiple electrically conductive layers that define a working electrode and a counter electrode disposed and/or arranged according to a two-electrode configuration. In the two-electrode configuration, the working electrode can be configured to initiate a chemical reaction of interest, while the counter electrode can be configured to complete an electrical circuit allowing charge to flow through and maintain a constant interfacial potential with the working electrode. Alternatively, in some embodiments, the electrode 120 can include multiple electronically conductive layers that define a working electrode, a counter electrode, and/or a reference electrode disposed and/or arranged according to a three-electrode configuration. In the three-electrode configuration, the working electrode can be configured to initiate the chemical reaction of interest, the counter electrode can be configured to pass an electrical current needed to balance the current observed at the working electrode, and the reference electrode can be configured to provide a reference in measuring and controlling the potential of the working electrode.

In some embodiments, the electrode 120 can include a working electrode, a counter electrode and a reference electrode conforming to any suitable shape, size, and/or geometry. In some embodiments, the electrode 120 can include a working electrode, a counter electrode, and a reference electrode, with each electrode having the same shape (e.g., a circular shape, rectangular shape, square shape, triangular shape, disc, polyhedral shape or any other geometrical shape). In other embodiments, the electrode 120 can include a working electrode, a counter electrode, and a reference electrode, with each electrode having a different shape. For example, in some embodiments, the electrode 120 can include a working electrode having a circular shape, a counter electrode having a rectangular shape, and a reference electrode having a square shape. In some embodiments, the electrode 120 can include a working electrode, a counter electrode and a reference electrode disposed in an irregular shape. In some embodiments, the size and/or the shape of the electrode 120 can be selected to facilitate electrochemical analysis of biological samples that can only be obtained in very small quantities and/or sample volumes. For example, in some embodiments, the electrode 120 can include a working electrode shaped as a circle or any other suitable geometrical shape having a cross-sectional area similar to the cross-sectional area generated by a low volume (e.g., 0.1 μL to 2 μL droplet) sample of a biological sample. In some embodiments, the size and/or the shape of the electrode 120 can be configured to improve the portability of the biosensor 100 and the related sample processing unit 170 and electrochemical testing unit 180.

In some embodiments, the electrode 120 can include a working electrode, counter electrode, and a reference electrode configured to have small sizes and compact footprint such that multiple biosensor 100 structures can be integrated into a single device and/or chip, allowing ultrasensitive multiplex detection of target species present in biological samples at low concentrations.

In some embodiments, the electrode 120 can be a screen-printed electrode strip comprising a working electrode, a counter electrode, and a reference electrode disposed on a support, e.g., a paper, plastic, and/or ceramic support. The working electrode, counter electrode, and reference electrode can be made of any suitable conductive material including gold (Au), platinum (Pt), silver (Ag), carbon (C), carbon nanotubes (CNT), graphene and the like. As described above, the size, and/or shape of the working electrode, counter electrode and/or reference electrode can be selected to facilitate conducting electrochemical analysis of various volumes of biological samples. For example, in some embodiments, the electrode 120 can include a working electrode, counter electrode, and/or reference with an active area (e.g., the area involved in the electron-transferring electrochemical reactions) sized to detect the target species utilizing sample volumes of no more than 1 μL, no more than 2 μL, no more than 5 μL, no more than 10 μL, no more than 20 μL, no more than 50 μL, no more than 100 μL, no more than 200 μL, no more than 500 μL, no more than 1 mL, no more than 2 mL, no more than 5 mL, no more than 10 mL, no more than 20 mL, no more than 30 mL, no more than 50 mL, inclusive of all values and ranges therebetween. In some embodiments, the electrodes can include a working electrode with an active area sized to detect target species utilizing sample volumes of at least about 4 mL, at least about 3 mL, at least about 1 mL, at least about 900 μL, at least about 750 μL, at least about 500 μL, at least about 250 μL, at least about 200 μL, at least about 100 μL, at least about 75 μL, at least about 50 μL, at least about 20 μL, at least about 10 μL, at least about 5 μL, at least about 2 μL, inclusive of all values and ranges therebetween. Combinations of the above referenced ranges for the sample volumes that the biosensor 100 can analyze are also possible (e.g., a sample of at least about 40 μL to no more than about 2 mL or a sample of at least about 100 μL to no more than about 900 μL).

In some embodiments, the electrode 120 can be configured to be disposable. That is, the electrode 120 can be configured to conduct electrochemical analysis of a biological sample and then be disposed of. Alternatively, in other embodiments, the electrode 120 can be configured to be reusable. In such embodiments, the electrode 120 can be configured to conduct a first electrochemical analysis of a biological sample, and then be subject to one or more conditioning steps such as cleaning, water and/or buffer resining, heating and cooling treatments and the like, to condition the electrode 120 to conduct a second electrochemical analysis of a biological sample.

The anchor layer 130 can be any suitable layer and/or coating disposed on the electrode 120 and configured to (1) be immobilized to the electrode 120 and (2) bind, conjugate, attach, and/or tether one or more components of the biosensor 100 to the anchor layer 130. In some embodiments the anchor layer 130 can include bifunctional molecules and/or species comprising a first chemical functionality and a second chemical functionality. The first chemical functionality can be configured to interact with the electrode 120 to immobilize and/or secure the anchor layer 130 to the electrode 120. The second chemical functionality can be configured to interact with surface functional groups present on the one or more components of the biosensor 100 to bind, conjugate, attach, and/or tether the one or more components of the biosensor 100 to the anchor layer 130. In some embodiments, the chemical functionalities (e.g., the first chemical functionality or the second chemical functionality) interact with the electrode 120 and with the surface functional groups present in the one or more components of the biosensor 100 via physical interactions that rely on ionic attraction (e.g., interactions between a negatively charged electrode 120 and a positively charged anchor layer 130), hydrophobic-hydrophilic interactions, and/or dative binding (e.g., coordinate covalent bonding) between the electrode 120 and one or more components of the anchor layer 130.

In some embodiments, the chemical functionalities (e.g., the first chemical functionality or the second chemical functionality) interact with the electrode 120 and with the surface functional groups present in the one or more components of the biosensor 100 via chemical reactions that form strong covalent bonds, immobilizing the anchor layer 130 to the electrode 120, and anchoring the one or more components of the biosensor 100 such as the linker 140 to the anchor layer 130. For example, in some embodiments, the anchor layer 130 can include bifunctional molecules and/or species having a first chemical functionality consisting of sulfur-containing groups that react chemically (via chemisorption) with a metal electrode 120 creating strong metal-sulfur bonds (M-S bonds) on the surface of the electrode 120. In some implementations, the first chemical functionality can include sulfur containing groups such as thiol or sulfhydryl group (R—SH), disulfide (R—S—S—R), and/or sulfide (R—S—R) groups, (with R representing a suitable substituent) which can react chemically with, for example, a gold electrode 120 to create strong gold-sulfur (Au—S) bonds on the surface of the electrode 120, or with a silver electrode 120 to create strong silver-sulfur (Ag—S) bonds on the surface of the electrode 120. The bifunctional molecules and/or species can also include a second chemical functionality comprising reactive functional groups such as carboxylic acid, alcohol, aldehyde, ketone, amine, and/or epoxide that can bind, conjugate, attach, and or tether other components of the biosensor 100 to the anchor layer 130 via chemical reactions that produce strong covalent bonds.

In some embodiments, the anchor layer 130 can include bifunctional molecules and/or species including n-alkanethiols that have a first chemical functionality comprising thiol groups that can be covalently bound to a metal electrode 120, and a second chemical functionality comprising carboxylic acid functional groups that can bind, conjugate, attach, and/or tether other components of the biosensor 100 to the anchor layer 130. For example, in some embodiments, the anchor layer 130 can include n-alkanethiols such as thioglycolic acid (TGA, $HS[CH_2]COOH$), 3-mercaptopropionic acid ($HS[CH_2]_2COOH$), 4-mercaptobutyric acid (e.g., $HS[CH_2]_3COOH$), 6-mercaptohexanoic acid (e.g., $HS[CH_2]_5COOH$), 8-mercaptooctanoic acid (e.g., $HS[CH_2]_7$ COOH), 11-mercaptoundecanoic acid (e.g., $HS[CH_2]_{10}COOH$) and/or 16-mercaptohexadecanoic acid (e.g., $HS[CH_2]_{15}COOH$). In some embodiments, the anchor layer 130 can include a single type of alkanethiol molecule configured to bind to the surface of a metal electrode 120. In other embodiments, the anchor layer 130 can include multiple alkanethiol molecules configured to bind to the surface of a metal electrode 120.

In some embodiments, the anchor layer 130 can include polyethylene glycol molecules functionalized with thiol groups (e.g., Thiol-PEG molecules, $HSCH_2CH_2O$—$[CH_2CH_2O]_n$ $CH_3$) that can react with a metal electrode 120 to produce strong metal-sulfur bonds on the surface of the metal electrode 120. The Thiol-PEG molecules can have n ethylene glycol monomeric units and include a carboxyl terminated group (e.g., Thiol-PEG$_n$-acid, $HSCH_2CH_2O$—$[CH_2CH_2O]_n$ COOH) that can bind, attach, and or tether other components of the biosensor 100 to the anchor layer 130. For example, in some embodiments, the anchor layer 130 can include Thiol-PEG$_3$-acid molecules ($HSCH_2CH_2O$—$[CH_2CH_2O]_3COOH$), Thiol-PEG$_4$-acid molecules $HSCH_2CH_2O$—$[CH_2CH_2O]_4COOH$), Thiol-PEG$_8$-acid molecules $HSCH_2CH_2O$—$[CH_2CH_2O]_8$ COOH), Thiol-PEG$_{12}$-acid molecules $HSCH_2CH_2O$—$[CH_2CH_2O]_{12}COOH$), and the like.

In some embodiments, the anchor layer 130 can be a self-assembled monolayer (SAM) and/or include bifunctional molecules and/or species configured to form a SAM on the electrode 120. For example, in some embodiments, the anchor layer 130 can include bifunctional molecules and/or species that have a first chemical functionality and a second chemical functionality as described above, and a spacer consisting of a linear hydrocarbon chain attached to the first chemical functionality and to the second chemical functionality (separating and/or spacing the first chemical functionality from the second chemical functionality), and configured to be oriented for example perpendicularly to the surface of the electrode 120 producing densely packed arrays of bifunctional molecules and/or species that cover the surface of the electrode 120. Said another way, the spacer can have two opposite ends chemically linked, bound and/or coupled to the first chemical functionality and to the second chemical functionality, and can be configured to facilitate alignment of the bifunctional molecules and/or species bound to the surface of the electrode 120 by orienting the bifunctional molecules and/or species perpendicularly or at an angle from the surface in a parallel manner through tail-tail interactions such as Van der Waals interactions, repellent, steric and/or electrostatic forces, resulting in highly ordered and oriented monomolecular layers. For example, in some embodiments, the anchor layer 130 can include bifunctional molecules and/or species including polyethylene glycol molecules functionalized with thiol groups and acid functionalities (Thiol-PEG$_n$-acid), where the length of the polyethylene unit (PEG$_n$) is selected to facilitate the formation of densely packed SAM. Similarly, in some embodiments, the anchor layer 130 can include bifunctional molecules and/or species including carboxy n-alkanethiols (e.g., $HS[CH_2]_nCOOH$) in which the length of the alkyl chain $[CH_2]_n$ is selected to facilitate the formation of densely packed SAM.

In some embodiments, the anchor layer 130 can include bifunctional molecules and/or species including disulfide molecules conforming to the chemical structure HOOC—R—S—S—R—COOH which have a first chemical functionality comprising disulfide groups that can be covalently bound to a metal electrode 120, a second chemical functionality comprising carboxylic acid functional groups that can bind, conjugate, attach, and/or tether other components of the biosensor 100 to the anchor layer 130, and where R can be an alkyl or and aryl substituent. For example, in some embodiments, the anchor layer 130 can include n-disulfide molecules such as 2-carboxyethyl disulfide (also referred to as 3,3' dithiodipropionic acid), 3-carboxypropyl disulfide, 5-carboxypentyl disulfide, 10-carboxydecyl disulfide, 2-carboxyphenyl disulfide and the like.

Figure 2A:
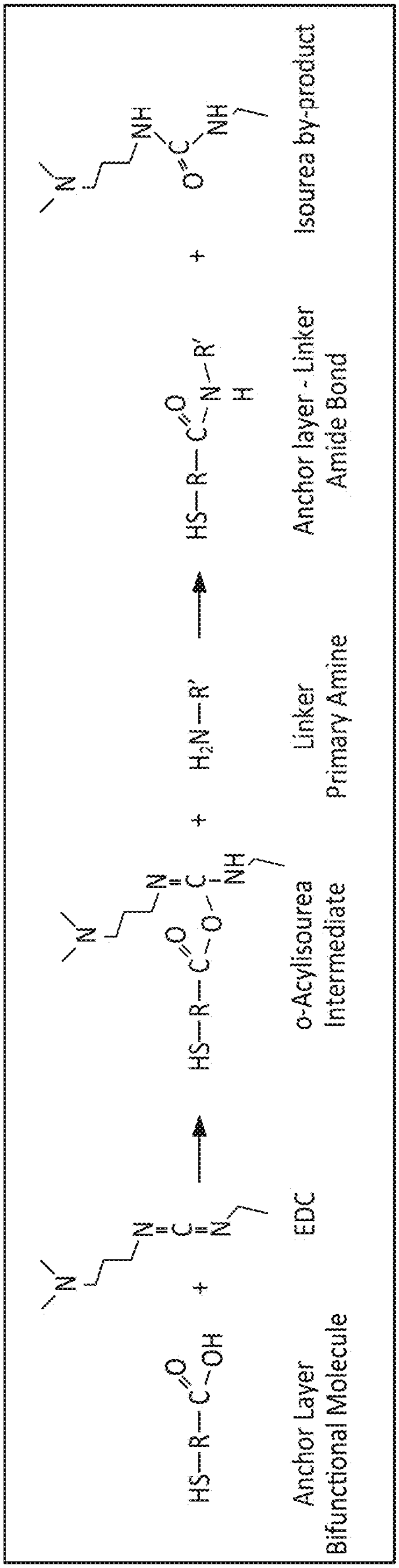
FIGS. 2A and 2B are schematic illustrations of chemical reactions between carboxylic functional groups of an anchor layer and primary amines of a linker of an electrochemical biosensor, according to an embodiment.

As described above, the anchor layer 130 can include bifunctional molecules and/or species having a second chemical functionality comprising carboxylic acid functional groups that can form covalent bonds with primary amines present in one or more components of the biosensor 100 to bind, conjugate, attach, and/or tether those components of the biosensor 100 to the anchor layer 130. In some embodiments, the carboxylic acid functional groups can be configured to react with primary amines with the aid of a carbodiimide additive via a condensation reaction that yields strong amide bonds. For example, in some embodiments the anchor layer 130 can include bifunctional molecules and/or species having a carboxylic acid functionality (COOH) that can react with 1-Ethyl-3-(3-dimethylaminopropyl) carbodiimide (EDC) additive to produce an o-Acylisourea unstable intermediate species. The o-Acylisourea intermediate can then react with primary amines ($H_2N$—R') present on the surface of a components of the biosensor 100 such as the linker 140, to produce a stable amide bond that binds, conjugates, attaches, and/or tethers the linker 140 to the anchor layer 130, and produce an isourea byproduct, as shown in FIG. 2A.

Figure 2B:
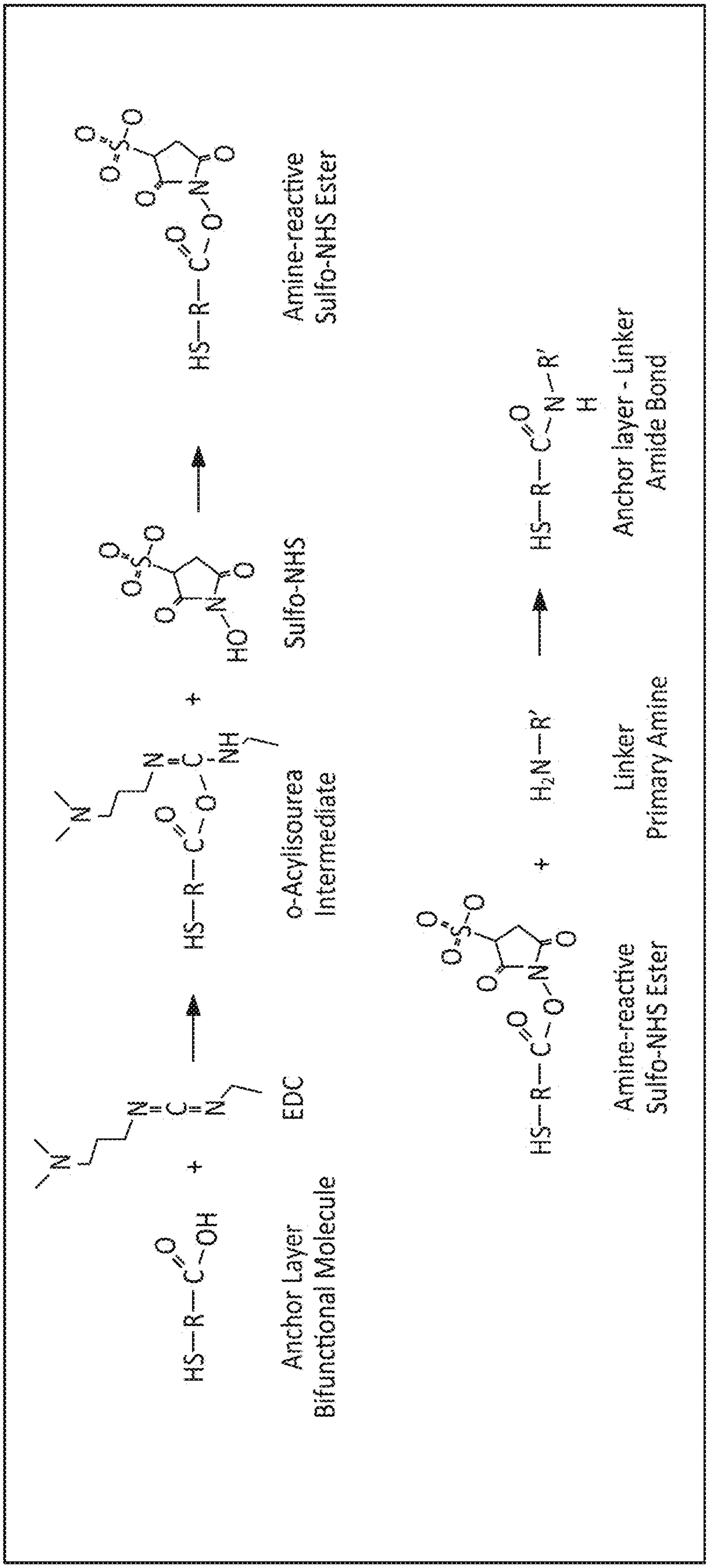

In other embodiments, the carboxylic acid functional groups can be configured to react with primary amines with the aid of a carbodiimide additive such as EDC and additional additives such as N-hydroxysuccinimide (NHS) or a water-soluble sulfonated analogue of NHS (Sulfo-NHS). For example, in some embodiments, the anchor layer 130 can include bifunctional molecules and/or species having a carboxylic acid functionality (COOH) that can react with 1-Ethyl-3-(3-dimethylaminopropyl) carbodiimide (EDC) to produce an o-Acylisourea unstable intermediate species. The o-Acylisourea intermediate can then incorporate the NHS to the carboxyl functionality producing an amine reactive sulfo-NHS ester intermediate that exhibits higher stability than the o-Acylisourea intermediate. The amine reactive sulfo-NHS ester intermediate can then react at physiologic pH (e.g., pH ~7.4) with primary amines ($H_2N$—R') present on the surface of a component of the biosensor 100 such as the linker 140, producing a stable amide bond that binds, conjugates, attaches, and/or tethers the linker 140 to the anchor layer 130, as shown in FIG. 2B.

The linker 140 can be any suitable component and/or chemical species configured to bind, conjugate, attach, and/or tether to second chemical functionality of the anchor layer 130. The linker 140 can also be configured to exhibit a strong affinity, binding strength, and/or strong chemical interaction towards a recognition component 150 such that the linker 140 can bind, conjugate, attach, and/or tether the recognition component 150 to produce linker 140—recognition component 150 conjugates. The strong affinity binding strength, and/or strong chemical interaction of the linker 140 towards a recognition component 150 can be characterized by a dissociating constant of a linker 140—recognition component 150 conjugate. For example, in some embodiments the linker 140—recognition component 150 conjugates can have a dissociating constant of at least about $2\times10^{-14}$, at least of about $3\times10^{-14}$, at least of about $5\times10^{-14}$, at least of about $8\times10^{-14}$, at least of about $1\times10^{-13}$, at least of about $5\times10^{-13}$, at least of about $8\times10^{-13}$, at least of about $1\times10^{-12}$, at least of about $2\times10^{-12}$, at least of about $5\times10^{-12}$, at least of about $9\times10^{-12}$, at least of about $1\times10^{-11}$ inclusive of all values and ranges therebetween.

In some embodiments, the linker 140 can include one or more biotin binding protein molecules such as streptavidin, avidin, neutravidin, and/or captavidin, which (a) have functional groups such as primary amines that react with the second chemical functionality of the anchor layer 130 to produce covalent bonds that attach the linker 140 to the anchor layer 130 as described above with reference to FIGS. 2A and 2B, and (b) comprise multiple binding sites that exhibit strong affinity towards a biotin-containing recognition component 150 to form avidin-biotin conjugates characterized by a conjugate dissociation constant of about $1.3\times10^{-15}$ M.

In some embodiments, the linker 140 can include streptavidin protein molecules having four biotin binding sites located in two opposites sites of the molecule, with the streptavidin protein molecules configured to be attached or anchored to the anchor layer 130 such that at least one of the biotin binding sites is oriented in a direction opposite to and/or away from the anchor layer 130. In other embodiments, the linker 140 can include streptavidin protein molecules having four biotin binding sites located in two opposites sites of the molecule, with the streptavidin protein molecules configured to be attached or anchored to the anchor layer 130 such that two biotin binding sites are oriented in a direction opposite to and/or away from the anchor layer 130.

In some embodiments, the linker 140 can include one or more biotin binding protein molecules such as streptavidin genetically modified to alter their biotin binding capacity and/or the number of biotin binding sites per molecule. In some embodiments, the linker 140 can include one or more streptavidin protein molecules having a reduced number of biotin binding sites per molecule, produced by altering streptavidin's homotetrameric structure via site-directed mutagenesis processes to produce monomeric structure streptavidin. For example, in some embodiments, the linker 140 can include streptavidin protein molecules that have been genetically modified through mutation of multiple residues such as tryptophan residues to alter the homotetrameric structure of streptavidin, which exhibits four biotin binding sites, and produce monomeric streptavidin exhibiting a single binding site.

The recognition component 150 can be any suitable component and/or chemical species couplable to the linker 140 and configured to selectivity bind a target species present in a biological sample (e.g., exhibit molecular recognition of the target species), via a noncovalent binding such as hydrogen bonding, metal coordination, hydrophobic forces, van der Waals forces, π-π interactions and/or electrostatic effects. The highly selective binding of the target species with the recognition component 150 can generate, induce, and/or modify electrical signals that can be used to detect, monitor and/or quantify the concentration of the target species present in the biological sample. In some embodiments, the recognition component 150 can include one or more affinity molecules and/or reagents such as antibodies (Ab) and/or aptamers that exhibit high selectivity (e.g., molecular recognition) towards a target species. The target species can include, for example, any antigen that can bind to monoclonal and/or polyclonal antibodies, toxins, proteins, complex molecules such as tetrahydrocannabinol (THC) secondary metabolites, and/or foreign substances associated with fungi, parasites, pathogenic bacteria and/or viruses. In some embodiments the recognition component 150 can comprise affinity molecules and/or reagents including, but not limited to norovirus VP1 antibodies, Severe Acute Respiratory Syndrome Coronavirus 2 (SARS-CoV-2) spike receptor binding domain (RBD) antibodies, Clustered Regularly Interspaced Short Palindromic Repeats CRISPR Associated protein 9 (CAS-9), interleukin 6 cytokine protein, interleukin 17A cytokine protein, and/or pepsin enzyme. The affinity molecules can selectively bind to specific antigens, toxins, and/or other foreign substances and generate, induce, and/or modify electrical signals which can be used to quantify the concentration of the target species present in the biological sample. The affinity molecules can also include biotin functional groups (e.g., a biotinylated recognition components 150) that can be coupled to biotin binding proteins present and/or included in the linker 140, effectively coupling the recognition component 150 to the linker 140, as described above. For example, in some embodiments, the recognition component 150 can include biotinylated CAS9 antibodies that can (1) exhibit specific interactions (e.g., molecular recognition) with CAS9 recombinant protein present in biological samples, and (2) bind, conjugate, attach and/or tether to biotin binding proteins present and/or included in the linker 140, as described above. The biotinylated CAS9 antibodies can bind the CAS9 recombinant protein, generating, altering and/or modifying electrical signals being exchanged between the electrode 120 and electrochemical testing unit 180 during, for example, a differential pulse voltammogram and/or a square wave voltammogram. The changes in the differential pulse voltammogram and/or the square wave voltammogram due to the CAS9 recombinant protein bound to the biotinylated CAS9 antibodies present in the recognition component 150 can be used to monitor, and/or quantify the concentration of CAS9 recombinant protein in biological samples such as human saliva samples.

In some embodiments, the recognition component 150 can include antibodies comprising a fragment antigen binding region (Fab) and a Fragment crystallizable region (Fc), with the Fab region including sites configured to bind specific antigens, as described above. In those embodiments, the recognition component 150 can be configured to be bound and/or conjugated to the streptavidin molecules of the linker 140 such that a substantial majority of the antibodies of the recognition component 150 assume a predetermined orientation with respect to the other components of the biosensor. For example, in some embodiments, the recognition component 150 can be configured to be bound and/or conjugated to the streptavidin molecules of the linker 140 such that a substantial majority of the antibodies assume a first orientation in which the Fc region is directly attached and/or conjugated to the linker 140 and the Fab region points away from the biosensor 100 (e.g., tail-on orientation). In other embodiments, the recognition component 150 can be bound and/or conjugated to the streptavidin molecules of the linker 140 such that a substantial majority of the antibodies assume a second orientation in which the Fab region is directly attached and/or conjugated to the linker 140, and the Fc region points away from the biosensor 100. In yet other embodiments, the recognition component 150 can be bound and/or conjugated to the streptavidin molecules of the linker 140 such that a substantial majority of the antibodies assume a third orientation in which a portion of the FAB region and a portion of the FC region are directly attached and/or conjugated to the linker 140 (e.g., side-ways orientation). In some embodiments, the antibodies of the recognition component 150 can be bound and/or conjugated to the streptavidin molecules of the linker 140 according to a combination of the first, second, and third orientations described above.

In some embodiments, the recognition component 150 can include one or more biotinylated polyclonal antibodies (pAbs) derived from animal sources. In some embodiments, the recognition component 150 can include one or more biotinylated monoclonal antibodies (mAbs) such as abciximab, adalimumab, ado-trastuzumab emtansine, alemtuzumab, alirocumab, atezolizumab, alirocumab, belimumab, cetuximab, denosumab, evolocumab, golimumab, infliximab-abda, natalizumab, necitumumab, ocrelizumab, palivizumab, ranibizumab, secukinumab, ustekinumab, guselkumab, benralizumab, and the like. In some embodiments, the recognition component 150 can include combinations of biotinylated polyclonal antibodies (pAbs) and biotinylated monoclonal antibodies.

In some embodiments, the biosensor 100 can optionally include a visualization component 160, as shown in FIG. 1. The visualization component 160 is configured to be attached and/or coupled to a component of the biosensor 100 such as the anchor layer 130 and/or the recognition component 150, and emit a fluorescent signal (in response to an excitation signal) that can be detected with a standard imaging device, allowing characterization of the distribution, orientation, surface density, and/or coverage of the component of the biosensor (e.g., the anchor layer 130 and/or the recognition component 150) on the biosensor 100. The visualization component 160 can include one or more optical elements such as a fluorescent dye, protein, and/or probe configured to absorb light and emit, in response to the absorbed light, a fluorescence signal which can be detected and/or imaged by any suitable detector such as a CCD detector, EM-CCD detector, and/or a CMOS detector. In some embodiments, the visualization component 160 be tagged and/or conjugated to the recognition component 150 and can be used to image the biosensor 100 by standard microscopy techniques, thereby facilitating the characterization of the recognition component 150 on the biosensor 100. For example, in some embodiments, the visualization component 160 can include Alexa Fluor 488 fluorescent probes tagged to the recognition component 150 of the biosensor 100 and configured to be illuminated with a suitable wavelength light source (e.g., 485-500 nm) to induce a fluoresce emission response from the Alexa Fluor 488 fluorescent probes that can be detected (at an emission peak of 519 nm) and imaged by a detector. The images of the visualization component 160 recorded by the detector can be used to characterize the distribution, orientation, surface density, and/or coverage of the recognition component 150 on the biosensor 100.

In some embodiments, the visualization component 160 be tagged and/or conjugated to the anchor layer 130 and can be used to image the biosensor 100 by standard microscopy techniques, thereby facilitating the characterization of the anchor layer 130. For example, in some embodiments, the visualization component 160 can include green fluorescent protein (GFP) conjugated to the anchor layer 130 of the biosensor 100 via interactions between the second chemical functionality of the anchor layer 130 and surface functional groups present on the GFP. In such embodiments, the visualization component 160 can be illuminated with a suitable wavelength light source (e.g., 480-495 nm) to induce a fluoresce emission response from the GFP that can be detected (at an emission peak of 509 nm) and imaged by a detector. The images of the visualization component 160 recorded by the detector can be used to characterize the distribution, surface density, and/or coverage of the anchor layer 130 on the biosensor 100.

In some embodiments, the visualization component 160 can include a single type of fluorescent dye, protein, and/or probe configured to be coupled to a component of the biosensor 100 to absorb light and emit a fluorescence response at a suitable range of wavelengths, thereby facilitating the characterization of the components of the biosensor 100 such as, for example, the anchor layer 130, the linker 140, and/or the recognition component 150. For example, in some embodiments, the visualization component 160 can include a fluorescent dyes, protein, and/or probe such as Pacific Blue, Alexa Fluor 488, Alexa Fluor 546, Alexa Fluor 633, FITC, Rhodamine 110, Rhodamine 123, Cy2, Cy5, DayLight 350, DayLight 405, Coumarin, DAPI, Marina Blue, CFP, eCFP, BOPRO-1, GFP, DTAF, CFDA, FITC, Acridine orange, and the like.

In some embodiments, the visualization component 160 can include multiple types of fluorescent dyes, proteins, and/or probes configured to be coupled to specific component of the biosensor 100 to absorb light and emit fluorescence responses at different wavelengths, thereby facilitating multiplexing, e.g., the simultaneous characterization of one or more components of the biosensor 100. In such embodiments, the visualization component 160 can include fluorescent dyes, proteins, and/or probes selected due to their non-overlapping excitation wavelengths and/or emission wavelengths. For example, in some embodiments, the visualization component 160 can include Alexa 488 fluorescence probes tagged to a first portion of the recognition component 150 which includes a first type of antibody, and Alexa 555 probes tagged to a second portion of the recognition component 150 which includes a second type of antibody. Exposure of the visualization component 160 to a light source having an excitation wavelength including 493 nm (e.g., the excitation peak wavelength for Alexa 488) results in absorption of light by the Alexa 488 fluorescence probes tagged to the first portion of the recognition component 150 and emission of fluorescence at a maximum emission wavelength of 519 nm. Similarly, exposure of the visualization component 160 to a light source having an excitation wavelength including 553 nm (e.g., the excitation peak wavelength for Alexa 555) results in absorption of light by the Alexa 555 fluorescence probes tagged to the second portion of the recognition component 150 and emission of fluorescence at a maximum emission wavelength of 568 nm. The fluorescence emission of the Alexa 488 and the Alexa 555 probes can be captured by suitable detectors and can be imaged with the aid of standard microscopy techniques to characterize the distribution, orientation, surface density, and/or coverage of the first portion of the recognition component 150 and the second portion of the recognition component 150 on the biosensor 100.

The sample processing unit 170 can be any suitable structure configured to receive, house, and/or store, biological samples comprising target species suitable for electrochemical analysis and/or quantification with the biosensor 100. In some embodiments, the sample processing unit 170 can be a receptacle that defines one or more interior volumes, compartments, and/or chambers in which biological samples can be received, housed, and/or stored prior to, during and/or after their electrochemical analysis with the biosensor 100. The sample processing unit 170 can be any suitable shape, and/or form. In some embodiments, the sample processing unit 170 can be a three-dimensional shape having a length and any suitable cross-sectional area including for example, circular, oval, square, rectangular, and/or other polygonal cross-sectional area. In some embodiments, the sample processing unit 170 can be a three-dimensional shape include multiple portions, with each portion having a length and any suitable cross-sectional area. In some embodiments, the sample processing unit 170 can include multiple portions that can be coupled and/or assembled together to form one or more interior volumes, compartments, and/or chambers for receiving biological samples. That is, in some embodiments, the sample processing unit 170 can be modular. Alternatively, in other embodiments, the sample processing unit 170 can be made of a monolithic structure.

In some embodiments, the sample processing unit 170 can be a receptacle that defines a single interior volume, compartment, and/or chamber in which a biological sample can be housed, and/or stored. In other embodiments, the sample processing unit 170 can be a receptacle that defines multiple interior volumes, compartments, and/or chambers suitable for receiving, housing, and/or storing multiple biological samples simultaneously. Alternatively, and/or optionally, in some embodiments the sample processing unit 170 can include multiple interior volumes, compartments, and/or chambers, with each compartment being configured to contain a biological sample (or a portion thereof) for a period of time to facilitate conducting one or more sample processing and/or sample preconditioning steps prior to the biological sample electrochemical analysis via the electrochemical testing unit 180. For example, in some embodiments, the sample processing unit 170 can include a first compartment configured to accommodate and/or receive a biological sample (or a portion thereof) for a period of time in order to conduct one or more processing steps such as mixing one or more reagent and/or additive (e.g., a reporter molecule, a buffer solution, and pH indicator, a rheology modifier and the like), heating the biological sample, cooling the biological sample, and/or filtrating the biological sample, and a second receptacle configured to receive and/or accommodate the biological sample after the biological sample is processed and/or pre-treated in the first receptacle.

In some embodiments, the sample processing unit 170 can include multiple interior volumes, compartments, and/or chambers, with each compartment being configured to contain either a biological sample (or a portion thereof) or one or more chemical reagents and/or additives used to conduct electrochemical analysis of biological samples with the biosensor 100 such as for example, a reporter molecule, a buffer solution, and pH indicator, a rheology modifier, a catalyst, and the like. In some implementations, multiple interior volumes, compartments, and/or chambers of the sample processing unit can be fluidically coupled via microfluidic channels (not shown). Said in other words, in some implementations the sample processing unit can include multiple microfluidic channels configured to couple fluidically one or more interior volumes, compartments, and/or chambers configured to receive biological samples, with one or more interior volumes, compartments, and/or chambers configured to receive chemical reagents and/or additives such as a reporter molecule, a buffer solution, and pH indicator, a rheology modifier, a catalyst, and the like, which may be used to conduct electrochemical analysis of biological samples with the biosensor 100.

In some embodiments, the sample processing unit 170 can be configured to be coupled to one or more external components to facilitate transferring biological samples from the external component to a receptacle of the sample processing unit 170. For example, in some embodiments, the sample processing unit 170 can include a receptacle configured receive and couple a syringe containing a biological sample, and a luer lock configured to be fluidically coupled to the syringe to allow a user to transfer at least a portion of the biological sample from the syringe to an interior volume, compartment, and/or chamber of the sample processing unit 170 by actuating the plunger of the syringe. In some embodiments, the sample processing unit 170 can further include a filtration membrane fluidically coupled to the syringe such that the user can actuate the plunger of the syringe to cause the biological sample stored in the syringe to flow from the syringe through the filtration membrane and into an interior volume, compartment, and/or chamber of the sample processing unit 170, effectively removing particles and/or other undesired components present in the biological sample. Moreover, in some embodiments, the syringe can also provide a fluidic pressure to the interior volume, compartment, and/or chamber the sample processing unit 170, ensuring an intimate contact between the biological sample the biosensor 100 during the electrochemical analysis of the biological sample.

As described above with reference to FIG. 1, the biosensor 100 can be removably coupled to the sample processing unit 170 to expose at least a portion of the biosensor 100 to biological samples stored, contained and/or housed within the sample processing unit 170. The biosensor 100 can be coupled to the sample processing unit 170 by any suitable means. In some embodiments, the sample processing unit 170 can include an opening, aperture, and/or a passage that can receive, convey and/or introduce the biosensor 100 within the interior volumes, compartments and/or chambers that hold the biological samples such that the biosensor 100 or a portion thereof becomes in physical contact with the biological sample to conduct electrochemical analysis of the biological sample. In such embodiments, a user can manually introduce the biosensor 100 through the opening of the sample processing unit 170 to expose the biosensor 100 or a portion thereof to the biological sample for electrochemical analysis.

In some embodiments, the sample processing unit 170 can include a cartridge 172 configured to receive the biosensor 100 and expose at least a portion of the biosensor 100 to biological samples stored on the sample processing unit 170. In some embodiments, the cartridge 172 can be further configured to electrically couple the biosensor 100 to the electrochemical testing unit 180 to conduct electrochemical analysis of the biological samples stored on the sample processing unit 170. In yet other embodiments, the cartridge 172 can be further configured to record, store, analyze and/or process data generated by the electrochemical testing unit 180 during electrochemical analysis of biological samples, as further described herein.

The cartridge 172 can include any suitable structure configured to removably receive, secure and/or mechanically immobilize the biosensor 100 to the cartridge 172. The cartridge 172 can include an engineering fit, interference fit, press fit and/or friction fit configured to receive and immobilize at least a portion of the biosensor 100. For example, in some embodiments, the cartridge 172 can include an opening, cavity, slot or the like defining an interference fit that can secure a first portion of the biosensor 100 by friction, after a surface defining an opening of the cartridge 172 and the biosensor 100 are pushed together. In other embodiments, the cartridge 172 can include a threaded end or threaded portion that can be coupled to a similarly sized threaded end or threaded portion disposed on the biosensor 100 such that the biosensor 100 is secured and/or mechanically immobilized to the cartridge 172. Alternatively, in other embodiments, the biosensor 100 can be coupled to the cartridge 172 via one or more coupling mechanisms including, but not limited to screws, bolt fasteners, welding, brazing, adhesives, or any combination thereof.

The cartridge 172 can be further configured to be coupled to the sample processing unit 170 such that when the biosensor 100 is received, secured, and/or mechanically immobilized to cartridge 172, the cartridge 172 with the biosensor 100 secured to it, can be disposed within the interior volumes, compartments and/or chambers that hold biological samples to expose at least a portion of the biosensor 100 to the biological samples for their electrochemical analysis. In some embodiments, a first portion of the biosensor 100 can be received, secured and/or mechanically immobilized to the cartridge 172, and then the cartridge 172 with the biosensor 100 secured to it, can be removably coupled to the sample processing unit 170 such that a second portion of the biosensor 100, different from the first portion of the biosensor 100 is disposed within the interior volumes, compartments and/or chambers that hold the biological samples for electrochemical analysis.

In some embodiments, the cartridge 172 can be configured to be reusable. In such embodiments, the cartridge 172 can include an engineering fit, interference fit, press fit and/or friction fit configured to removably receive at least a portion of a first biosensor 100 to secure the first biosensor 100 to the cartridge 172 for a period of time, allowing the first biosensor 100 to be coupled to the sample processing unit 170, and be exposed to biological samples contained in the sample processing unit 170 with the purpose of determining the presence and/or concentration of target species via electrochemical analysis. Upon completion of the electrochemical analysis of biological samples, the cartridge 172 can be removed from the sample processing unit 170, and the first biosensor 100 can be removed from the cartridge 172. The cartridge 172 can then be used to receive and secure a second biosensor 100 for further electrochemical analysis of biological samples.

In some embodiments, the sample processing unit 170 and/or the cartridge 172 can include an electromagnetic shield configured to block electromagnetic radiation and radio frequencies (e.g., RF shield) reducing the coupling of radio waves, electromagnetic fields, and electrostatic fields generated by external sources such a wireless fidelity (WI FI) network, mobile phones, short-range wireless communication devices (Bluetooth), and consumer electronic devices. The RF shield can include a field barrier made of conductive or magnetic materials that isolate the biosensor 100 from its surroundings, preventing evolution of noisy electrical signals during electrochemical analysis of a biological samples caused by external factors. The RF shield can be any suitable size and shape. In some embodiments, the RF shield can an enclosure made of one or more metals such as copper, brass, nickel, silver, steel, and tin. In some embodiments, the RF shield can be made of sheet metal, metal screen, and/or a metal foam. In some embodiments, the RF shield can include a plastic enclosure coated on the inside with a metallic ink consisting of a carrier material loaded with a suitable metal, typically copper or nickel, in the form of very small particulates.

In some embodiments, the cartridge 172 can include one or more additional components (not shown in FIG. 1) such as power source, and/or a control unit. The power source can be any suitable energy source and/or energy storage device. In some embodiments, the power source can include one or more rechargeable batteries. In some embodiments, the cartridge 172 can include one or more ports that enable connection between an external power source and one or more components of the cartridge 172. In some instances, the external power source can be used to directly power the components of the cartridge 172 and/or recharge the power source.

The control unit of the cartridge 172 can be configured to receive electrical signal(s) from and/or sending electrical signal(s) to the electrochemical testing unit 180, and/or an external device. The control unit can include a memory, a processor, and an input/output (I/O) device. The memory can be, for example, a random-access memory (RAM), a memory buffer, a hard drive, a database, an erasable programmable read-only memory (EPROM), an electrically erasable read-only memory (EEPROM), a read-only memory (ROM), and/or so forth. In some embodiments, the memory can store data generated and/or received by the electrochemical testing unit 180, or instructions received from an external device, which can be executed by the processor. Such instructions can be designed for example to identify data related to the biosensor 100 such as characteristics and/or features of the biosensor 100 or any of its components (e.g., the electrode 120, the anchor layer 130, the linker 140, the recognition component 150 and/or the visualization component 160), and/or record data related to the electrochemical analysis of a biological sample including date and/or time of the electrochemical analysis, duration of the electrochemical analysis, and/or data associated with the biological sample being tested.

The processor can be any suitable processing device configured to run and/or execute instructions as described above. The processor can be a general-purpose processor, a Field Programmable Gate Array (FPGA), an Application Specific Integrated Circuit (ASIC), a Digital Signal Processor (DSP), and/or the like. The input/output (I/O) device can include one or more components for receiving information and/or sending information to other components of the sample processing unit 170 and/or the electrochemical testing unit 180. In some embodiments, the I/O device can include a network interface that can enable communication between the control unit and one or more external devices, including, for example, an external user device (e.g., a mobile phone, a tablet, a laptop) and/or other compute devices (e.g., a local or remote computer, a server, etc.). The network interface can be configured to provide a wired connection with the external device, e.g., via a port or firewall interface. Alternatively, or optionally, the network interface can be configured to communicate with the external device via a wireless network (e.g., Wi-Fi, Bluetooth®, low powered Bluetooth®, Zigbee and the like). In some embodiments, the communication interface can also be used to recharge the power source (e.g., the rechargeable battery).

The electrochemical testing unit 180 can be any suitable electrochemistry workstation capable of generating electrical signals and conducting electrochemical characterization techniques and/or methods to determine the presence and/or concentration of target species. The electrochemical testing unit 180 can be electrically coupled to the biosensor 100 to conduct electrochemical analysis of biological samples. The biosensor 100 can include one or more electrically conductive surfaces and/or terminals that can be placed in direct electrical contact with the electrochemical testing unit 180 to exchange electrical signals and thus conduct electrochemical analysis. For example, in some embodiments the biosensor 100 can be coupled to the electrochemical testing unit 180 via one or more electrical leads, wires, cables and the like welded to the biosensor 100. In other embodiments, the biosensor 100 can include an electrically conductive surface configured to be electrically coupled to the electrochemical testing unit 180 with a clamp or a sprung metal clip with long serrated jaws (e.g., an alligator clamp) attached to a metallic wire such as copper, nickel, nickel-chromium (NiCr wire) or the like. In other embodiments, the biosensor 100 can include an electrically conductive surface configured to be electrically connected to a thick wire of a precious metal wire and/or inks such as silver, platinum and/or gold.

In some embodiments, the biosensor 100 can be electrically coupled to the electrochemical testing unit 180 via the cartridge 172 of the sample processing unit 170. In such embodiments, the cartridge 172 can electrically couple the biosensor 100 to the electrochemical testing unit 180 to send and receive electrical signals between the electrochemical testing unit 180 and the electrode 120, while at the same time mechanically couple the biosensor 100 to the sample processing unit 170 to expose the biosensor 100 to biological samples housed, and/or stored therein. The cartridge 172 can include an electrically conductive surface and/or terminal configured to receive a similarly shaped electrically conductive surface and/or terminal of the biosensor 100 to establish electrical contact (e.g., continuity). The cartridge 172 can also include a second electrically conductive surface and/or terminal that can be electrically coupled to the electrochemical testing unit 180, such that the electrochemical testing unit 180 and the biosensor 100 can be in electrical contact (e.g., continuity). For example, in some embodiments, the electrically conductive surface and/or terminal can be disposed within an opening, aperture, and/or slot of the cartridge 172 forming a port shaped and configured to receive a portion of the biosensor comprising a similar electrically conductive surface and/or terminal. In some embodiments, the electrically conductive surface and/or terminal of the cartridge 172 can include a spring-loaded mechanism configured to exert a force against the biosensor 100 to ensure continuous electrical contact and continuity between the electrode of the biosensor 100 and the cartridge 172. Similarly, the cartridge 172 can include a second electrically conductive surface and/or terminal electrically coupled to the electrochemical testing unit 180, such that the electrochemical testing unit 180 and the cartridge 172 are in electrical contact (e.g., continuity).

The electrochemical testing unit 180 can any suitable electrochemistry workstation capable of generating electrical signals to conduct potentiostat or galvanostat electrochemical characterization techniques and/or diagnostic tests such as cyclic voltammetry (CV), differential pulse voltammetry (DPV), square wave voltammetry, galvanostatic cycling (GC), galvanostatic or potentiostat intermittent titration techniques (GITT or PITT), and/or impedance spectroscopy (EIS). In some embodiments, the electrochemical testing unit 180 can incorporate software programing and/or algorithms configured to conduct predetermined tests and store a library of electrochemical response (e.g., signatures) associated with different biological samples and/or target molecules, facilitating the identification and monitoring the composition of biological samples of interest.

Figure 3A:
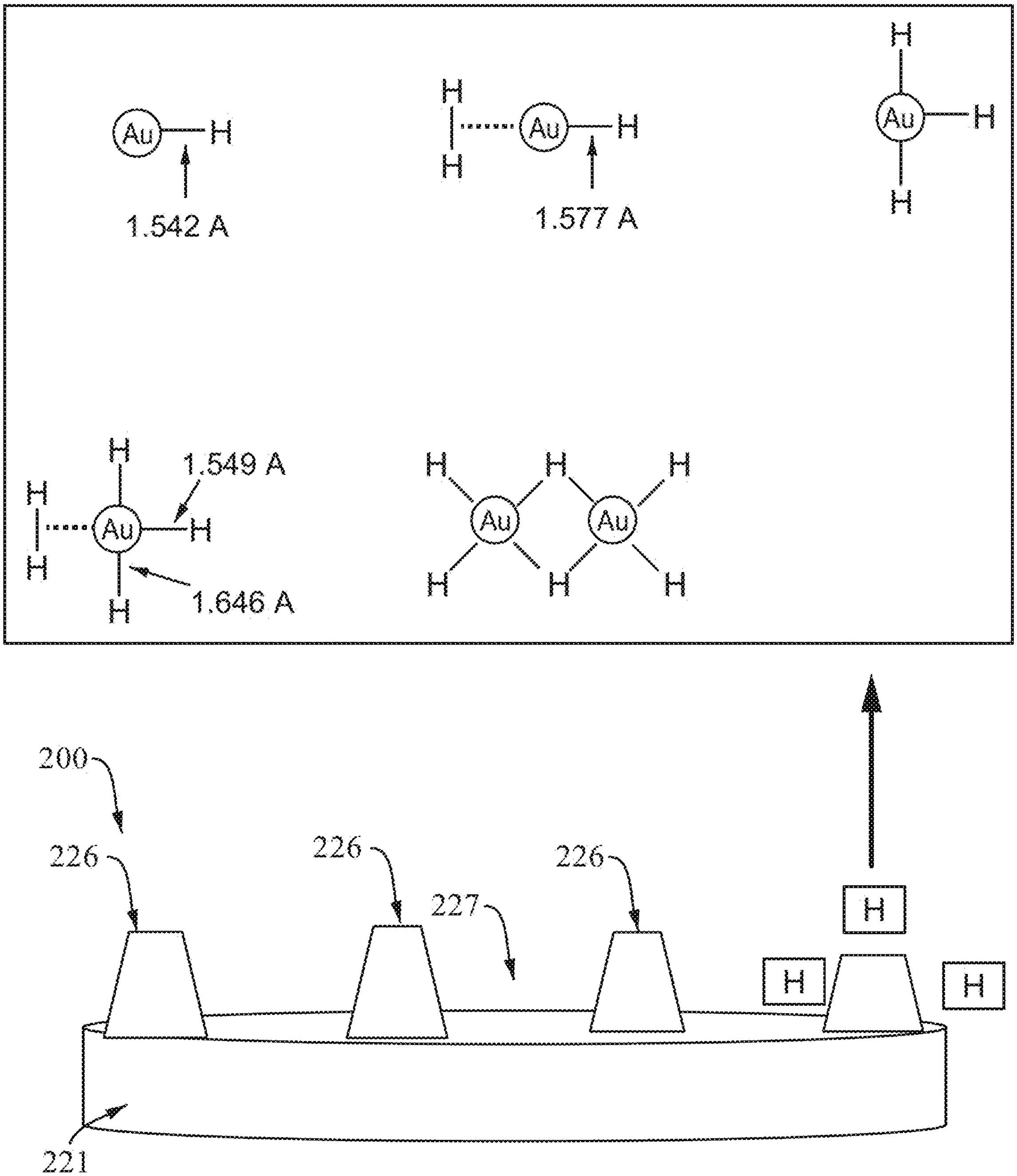
FIGS. 3A-3H are schematic illustrations of a procedure to fabricate an electrochemical biosensor according to an embodiment.

FIGS. 3A-3H show a schematic illustration of a procedure to fabricate an electrochemical biosensor 200 according to an embodiment. The electrochemical biosensor 200, which can also be referred to as the biosensor 200, can be similar to and/or substantially the same as one or more portions (and/or combination of portions) of the biosensor 100 described above with reference to FIG. 1. More specifically, the biosensor 200 can be substantially similar in at least form and/or function to the biosensor 100 described in detail above. Thus, portions and/or components of the biosensor 200 may not be described in further detail herein. FIG. 3A shows that the biosensor 200 includes a gold (Au) working electrode 221. The Au working electrode 221 can be subjected to one or more processing steps in order to fabricate the biosensor 200. For example, in some embodiments the Au working electrode 221 can be subjected to a first processing step, also referred to as a surface activation step, in which the Au working electrode 221 is treated according to one or more procedures to increase the surface chemical reactivity of the Au working electrode 221, expediting chemical reactions to bind, conjugate, attach, and/or tether one or more components of the biosensor 200. For example, in some embodiments, in the first processing step or activation step the Au working electrode 221 can be treated by etching a portion of the electrode to alter the topography of the electrode and introduce features, patterns, and or groves on the surface of the Au working electrode 221, as further described herein.

FIG. 3A shows in some embodiments the Au working electrode 221 can be exposed to a Laser to etch a portion of the electrode and form multiple features, patterns, and or groves 226 on the surface of the Au working electrode 221, surrounded by valleys 227. In some embodiments, the features, patterns, and or groves 226 on the Au working electrode 221 can be generated by using, for example, a blue Laser (e.g., a Laser that emits electromagnetic radiation with a wavelength of between 360 and 480 nm). The Au working electrode 221 can be etched to produce patterns, features, and/or grooves 226 of a predetermined shape and/or geometry. For example, in some embodiments the patterns, features, and/or grooves 226 can correspond to and/or resemble one or more geometries including, but not limited to a square, rhombus, parallelogram, diamond, bowtie, and/or pyramid shape. In some embodiments, the area of the Au working electrode 221 exposed to the etching procedure can represent and/or account for a percentage of the total area of the Au working 221 of at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, inclusive of all values and ranges therebetween. Said in other words, in some embodiments the patterns, features, and/or grooves 226 can disposed on a percentage of the total area of the Au working electrode 221 between about 30 to 95%. In some embodiments, the patterns, features, and/or grooves 226 can have a characteristics length (e.g., a dimension that defines the scale and/or size of the features 226) of at least about 20 nm, at least about 30 nm, at least about 40 nm, at least about 50 nm, at least about 60 nm, at least about 70 nm, at least about 80 nm at least about 90 nm, at least about 100 nm at least about 120 nm at least about 140 nm, at least about 160 nm, at least about 180 nm, or at least about 200 nm, inclusive of all values and ranges therebetween.

In some embodiments, as part of the first processing step the Au working electrode 221 can be treated by exposing one or more surfaces of the Au working electrode 221 to a solution containing strong oxidizing agents such as hydrogen peroxide ($H_2O_2$) to remove contaminants that may be adsorbed and/or deposited on the one or more surfaces of the Au working electrode 221. More specifically, in some embodiments the Au working electrode 221 can be treated with a $H_2O_2$ solution after the etching of patterns, features, and/or grooves 226 on the Au working electrode 221 described above. The etching of the patterns, features, and/or grooves 226 can generate contaminants including residues of plasticizer, polymers, fillers, hydrocarbons, paraffins and/or any other component of the support material on which the Au working electrode 221 is disposed. These contaminants can accumulate on the valleys 227 reducing the relative height of the features 226 measured with respect to the base of the Au working electrode 221 or with respect to an outer surface of the support material on which the Au working electrode 221 is disposed. This contaminants can interfere with the biosensor 200 fabrication procedure and/or the biosensor 200 performance. Without being bound by any particular theory, it is believed that the solutions containing $H_2O_2$ can react on the surface of the Au working electrode 221 dissolving and/or removing the contaminants and forming gold hydride (e.g., AuHn) species. FIG. 3 shows different types of gold hydride species that can be produced by the reaction of a gold atom with $H_2O_2$ molecules. The gold hydride species can include one or more gold-hydrogen (Au—H) bonds. In some instances, the gold hydride species can be incorporated on the gold lattice and increase the electrochemical activity of the Au working electrode 221. For example, FIG. 4A shows a chronoamperometry voltagram of a Au working electrode 221 which has been treated with a $H_2O_2$ solution and thus comprises gold hydride species. The voltagram in FIG. 4A shows the electric current response (e.g., discharge current) as a function of time obtained when the Au working electrode 221 is subjected to a constant electrical potential and/or operating voltage. The Au working electrode 221 of FIG. 4A produces an initial current of about 1.5 mA which decreases overtime as the gold hydrides are depleted from the surface of the Au working electrode 221. FIG. 4B shows a chronoamperometry voltagram recorded under the same operating conditions as that of the voltagram shown in FIG. 4A (e.g., same constant electrical potential and/or operating voltage), using a Au working electrode 221 which has not been treated with a $H_2O_2$ solution and thus does not comprises gold hydride species. The chronoamperometry voltagram of FIG. 4B shows the Au working electrode produces an initial current of about 0.12 mA which very rapidly decays reaching no current conditions and remains at that level for the duration for the experiment.

Figure 3B:
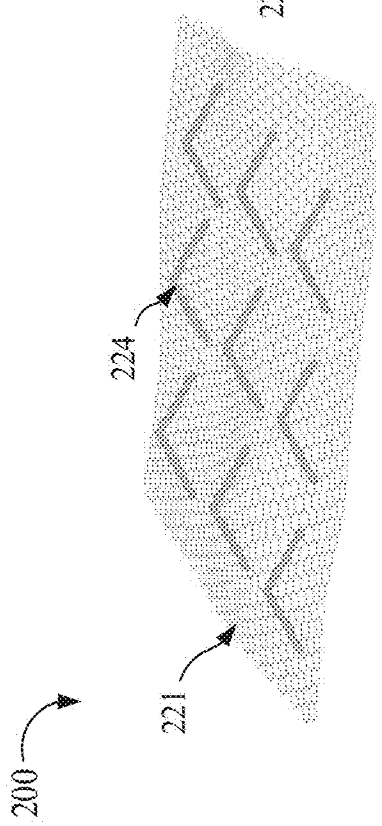
Figure 4A:
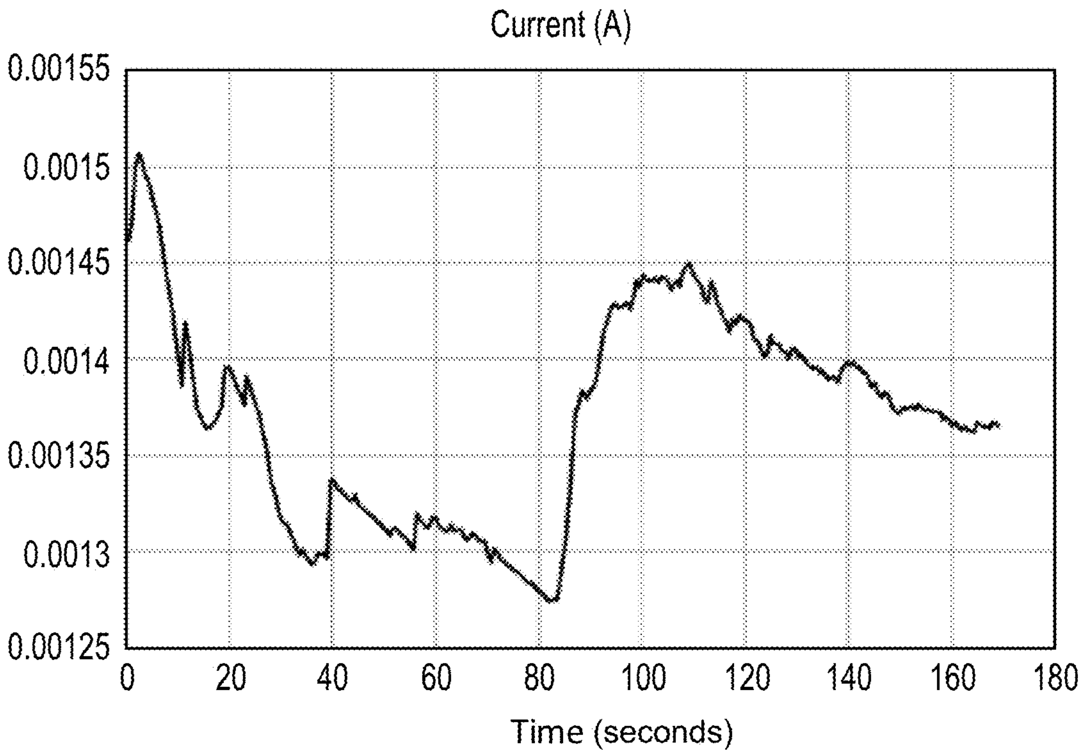
FIGS. 4A and 4B are chronoamperometry voltammograms of a gold (Au) working electrode which has been treated with a $H_2O_2$ solution (FIG. 4. A) and a gold (Au) working electrode which has not been treated with a $H_2O_2$ solution (FIG. 4. B), displaying the effect of gold hydrides on the electrochemical activity of the Au working electrode.
Figure 4B:
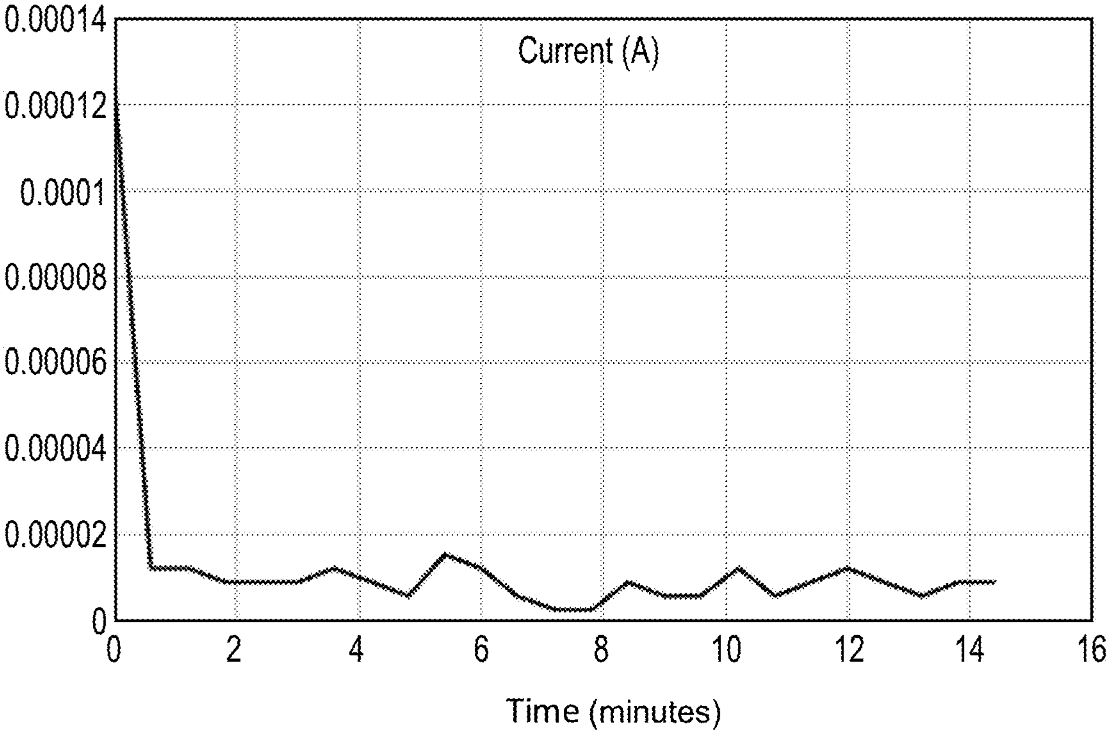

FIG. 3B shows a schematic representation of a Au working electrode 221 which can be subjected to one or more chemical treatments alternative to or complementary to the etching treatment described above, as part of the first processing step or surface activation step. For example, in some embodiments, the Au working electrode 221 can be treated by exposing a surface of the Au working electrode 221 to one or more etching solutions containing reagents such as potassium iodide (KI) and iodine ($I_2$). Without being bound by any particular theory, it is believed that the etching solutions containing reagents such as KI, and/or ($I_2$) can react with gold atoms bound to the surface of the Au working electrode 221 and remove and/or etch small amounts of gold as soluble gold iodine species (AuI), altering the surface topography of the Au working electrode 221 and generating for example, features such as a plurality of highly reactive Au nano ridges 224. In some embodiments, the Au nano ridges 224 generated on the surface of the Au working electrode 221 can have a length of at least about 20 nm, at least about 50 nm, at least about 60 nm, at least about 70 nm, at least about 80 nm, at least about 90 nm, at least about 100 nm, at least about 120 nm, at least about 140 nm, at least about 160 nm, at least about 180 nm, at least about 200 nm, at least about 250 nm, at least about 300 nm, inclusive of all values and ranges therebetween. In some embodiments, the Au nano ridges 224 generated on the surface of the Au working electrode 221 can have a length of no more than about 300 nm, no more than about 260 nm, no more than about 220 nm, no more than about 180 nm, no more than about 120 nm, no more than about 100 nm, no more than about 90 nm, no more than about 70 nm, no more than about 50 nm, or no more than 20 nm, inclusive of all values and ranges therebetween. Combinations of the above referenced length of the Au nano ridges 224 generated on the surface of the Au working electrode 221 are also possible (e.g., a length of at least about 80 nm to no more than about 150 nm, at least about 60 nm to no more than 300 nm). In some embodiments the Au nano ridges 224 generated on the surface of the Au working electrode 221 can have a width of at least about 15 nm, at least about 20 nm, at least about 15 nm, at least about 25 nm, at least about 30 nm, at least about 35 nm, at least about 40 nm, at least about 45 nm, at least about 50 nm, at least about 60 nm, at least about 75 nm, inclusive of all values and ranges therebetween. In some embodiments, the Au nano ridges 224 generated on the surface of the Au working electrode 221 can have a width of no more than about 75 nm, no more than about 60 nm, no more than about 50 nm, no more than about 40 nm, no more than about 35 nm, no more than about 30 nm, no more than about 25 nm, no more than about 20 nm, no more than about 15 nm, inclusive of all values and ranges therebetween. Combinations of the above referenced width of the Au nano ridges 224 generated on the surface of the Au working electrode 221 are also possible (e.g., a width of at least about 20 nm to no more than about 40 nm, at least about 15 nm to no more than 70 nm). In some embodiments, the Au working electrode 221 can be treated as part of the first processing step or activation step, by exposing the one or more surfaces of the Au working electrode 221 to solutions containing strong acids such as hydrochloric acid (HCl), and/or strong oxidants such as hydrogen peroxide ($H_2O_2$) to remove contaminants that may be adsorbed and/or deposited on the one or more surfaces of the Au working electrode 221, as described above with reference to the etching treatment. For example, in some embodiments the Au working electrode 221 can be treated by exposing a surface of the Au working electrode 221 to a $H_2O_2$ solution for a period of time of about 2 to 6 min.

In some embodiments, the volume of the $H_2O_2$ solution can be about 2 μL, about 4 μL, about 6 μL, about 8 μL, about 10 μL, about 15 μL, about 20 μL, about 30 μL, about 40 μL, or about 50 μL, inclusive of all values and ranges therebetween. In some embodiments, the concentration of $H_2O_2$ solution can be any suitable concentration, such as for example, 30% v/v $H_2O_2$. In some embodiments, the Au working electrode 221 can be rinsed with deionized water (DI) between successive exposures to the $H_2O_2$ solutions. For example, in some embodiments the Au working electrode 221 can be exposed to a first volume of a $H_2O_2$ solution for a first period time. The first volume of $H_2O_2$ solution can be removed from the surface of the Au working electrode 221 after completing the first period of time (e.g., by pipetting the $H_2O_2$ solution off the surface of the Au working electrode 221). The Au working electrode 221 can then be exposed to a volume of DI water to clean and/or rinse any contaminants and/or residue left on the surface of the Au working electrode 221. The DI water can then be removed and/or flushed away from the Au working electrode 221. Subsequently, the Au working electrode 221 can be exposed to a second volume of $H_2O_2$ solution for a second period of time. This $H_2O_2$ treatment can be repeated two or more times in order to facilitate activating the surface of the Au working electrode 221. Alternatively and/or complementary, in some embodiments the Au working electrode 221 can be treated by mechanical methods (e.g., sanding the surface of the Au working electrode 221 with an abrasive material) using a fine grit sanding material to score the surface of the Au working electrode 221 and increase the surface adhesion of the anchor layer 230 and/or other components of the biosensor 200.

Figure 3C:
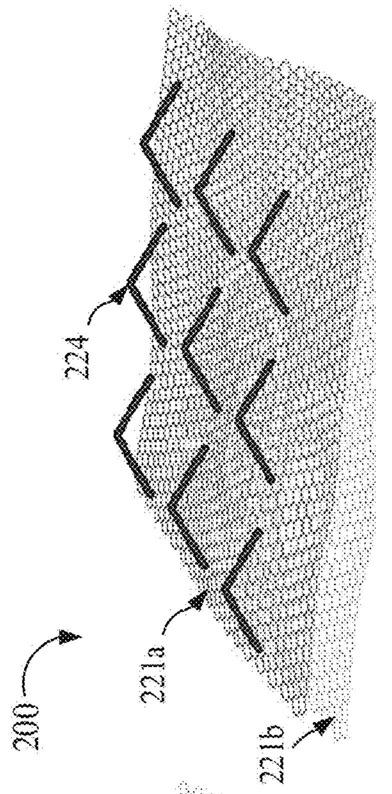

FIG. 3C schematically shows exposure of the Au working electrode 221 to the first processing step and/or surface activation step, which may include an etching treatment, a $H_2O_2$ treatment, a KI or I2 treatment, and/or a mechanical treatment, can produce a Au surface comprising features including nano ridges 224. FIG. 3C also depicts the first processing step can lead to the formation of an outer surface layer 221*a* of the Au working electrode 221 disposed above one or more interior layers 221*b* of the Au working electrode. In some embodiments, the activated outer surface layer 221*a* of the Au working electrode 221 can exhibit a bronze color characteristic of oxidized Au surfaces treated with $H_2O_2$ and/or other strong oxidizing reagents.

Figure 3D:
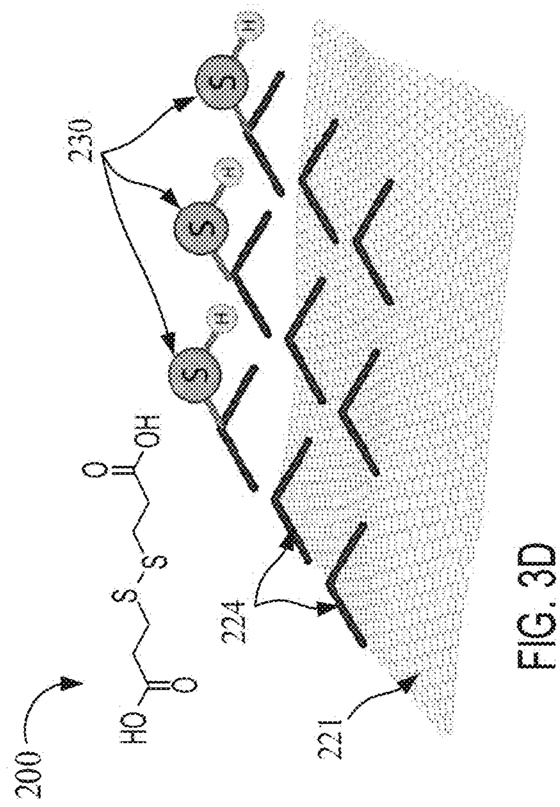

FIG. 3D shows a second processing step following the first processing step or surface activation step described above. In the second processing step, the Au working electrode 221 (including the activated surface layer 221, not shown) and the nano ridges 224 can be exposed to and/or coated with an anchor layer 230 with the purpose of immobilizing the anchor layer 230 to the Au working electrode 221 and providing surface functional groups that can be used to bind anchor, attach, and/or tether one or more components of the biosensor 200 to the anchor layer 230. In some embodiments, the Au working electrode 221 and nano ridges 224 can be exposed to the anchor layer 230 by disposing a small volume of a liquid solution comprising the anchor layer 230 and incubating the liquid solution for a period of time to allow the bifunctional molecules and/or species of the anchor layer 230 to react with the nano ridges 224 and bind the anchor layer 230 to the electrode 220. In some embodiments, the liquid solution comprising the anchor layer 230 can be disposed on the Au working electrode 221 and allow to cure for a predetermined period of time. For example, in some embodiments a volume of liquid solution comprising the anchor layer 230 can be disposed on the Au working electrode 221 for about 5 min, about 10 min, about 15 min, about 20 min, about 30 min, about 40 min, about 50 min, about 60 min, about 70 min, about 80 min, about 90 min, about 100 min, about 110 min, or about 120 min, inclusive of all values and ranges therebetween. In some embodiments, the volume of liquid solution comprising the anchor layer 230 can be disposed on the Au working electrode 221 while flowing a stream of nitrogen gas ($N_2$) to prevent contamination of the Au working electrode 221.

In some embodiments, the anchor layer 230 can be mixed with and/or diluted with one or more suitable buffer and then be disposed on the Au working electrode 221 for incubation. The buffer can be configured to maintain a stable and/or controlled pH during the immobilization of the anchor layer 230 to the Au working electrode 221. The buffer can include one or more aqueous buffers solutions such as PBS, HEPES, TRIS, PIPES, MES and the like, having a suitable concentration and/or buffer strength. In some embodiments, the buffer can have a concentration of no more than 2M, no more than 1M, no more than 500 mM, no more than 200 mM, no more than 100 mM, no more than 50 mM, no more than 25 mM, no more than 10 mM, no more than 5 mM, no more than 2 mM, no more than 1 mM, no more than 0.5 mM, no more than 0.2 mM, no more than 0.1 mM, no more than 0.08 mM, no more than 0.05 mM, inclusive of all values and ranges therebetween. In some embodiments, the buffer can have a concentration of at least 0.01 mM, at least 0.05 mM, at least 0.1 mM, at least 0.2 mM, at least 0.5 mM, at least 0.8 mM, at least 1 mM, at least 2 mM, at least 5 mM, at least 10 mM, at least 50 mM, at least 100 mM, at least 200 mM, at least 500 mM, at least 1M, at least 2 M inclusive of all values and ranges therebetween. Combinations of the above referenced ranges for the concentration of the buffer are also possible (e.g., a buffer of at least 0.2 mM to no more than 100 mM, or a buffer of at least 20 mM to no more than 1M).

As described above with reference to the anchor layer 130 in FIG. 1, the anchor layer 230 can include bifunctional molecules and/or species comprising a first chemical functionality (e.g., a thiol functional group) configured to interact with the Au working electrode 221 to immobilize and/or secure the anchor layer 230 to the Au working electrode 221, and a second chemical functionality (e.g., carboxylic acid) configured to interact with surface functional groups present on the one or more components of the biosensor 200 to bind, conjugate, attach, and/or tether the one or more components of the biosensor 200 to the anchor layer 230. FIG. 3C shows the anchor layer 230 can include 3 3' dithiodipropionic molecules which can cleave and/or split the S—S bond on the surface of the Au working electrode 221 producing two thiolated bifunctional molecules and/or species that can bind to the nano ridges 224 species via the thiol functionality and produce self-assembled monolayers (SAMs). That is, in some embodiments, the anchor layer 230 can be a self-assembled monolayer. In some embodiments, the anchor layer 230 can include one or more bifunctional molecules and/or species such as those described with reference to the anchor layer 130. For example, in some embodiments, the anchor layer 230 can include bifunctional molecules and/or species such as thioglycolic acid, 3-mercaptopropionic acid, 6-mercaptohexanoic acid, thiol-$PEG_3$-acid ($HSCH_2CH_2O$—$[CH_2CH_2O]_3COOH$), thiol-$PEG_8$-acid ($HSCH_2CH_2O$—$[CH_2CH_2O]_8COOH$), and the like.

Figure 3E:
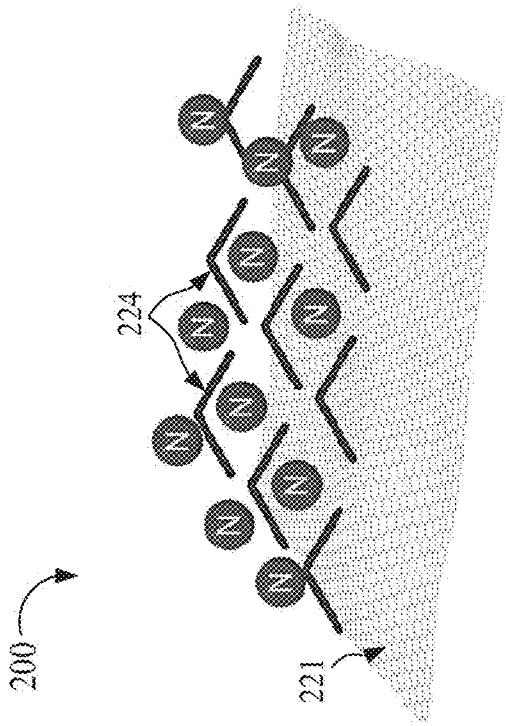

FIG. 3E schematically shows a third processing step following the exposure of the Au working electrode 221 to the anchor layer 230 described above with reference to FIG. 3D. In the third fabrication step, the nano ridges 224 covalently bound via thiol functional groups to the anchor layer 230 (not shown in FIG. 3E for simplicity) can be exposed to a stream of a high purity gas such as Nitrogen with the purpose of inducing electrostatic binding interactions between nitrogen and the thiol groups to protect the thiol groups from non-specific binding reactions with contaminants and/or unwanted species present in the environment surrounding the Au working electrode 221. FIG. 3E shows a schematic representation of Nitrogen electrostatically bound to the thiol groups on the Au working electrode 221 and the nano ridges 224. In some embodiments, high purity Nitrogen can be flown over the Au working electrode 221 at a low pressure for a period of time, such as for example at a pressure of 5 psi for 120 min, to ensure good contact between the thiol groups covalently bound to the Au surface 221 and nano ridges 224 and the Nitrogen stream. In some embodiments, the Au working electrode 221 with nano ridges 224 covalently bound via thiol functional groups to the anchor layer 230 can be exposed to a negative pressure chamber with the purpose of protecting the thiol groups from non-specific binding reactions and/or removing excess species not covalently bound to the surface of the Au working electrode 221.

Figure 3F:
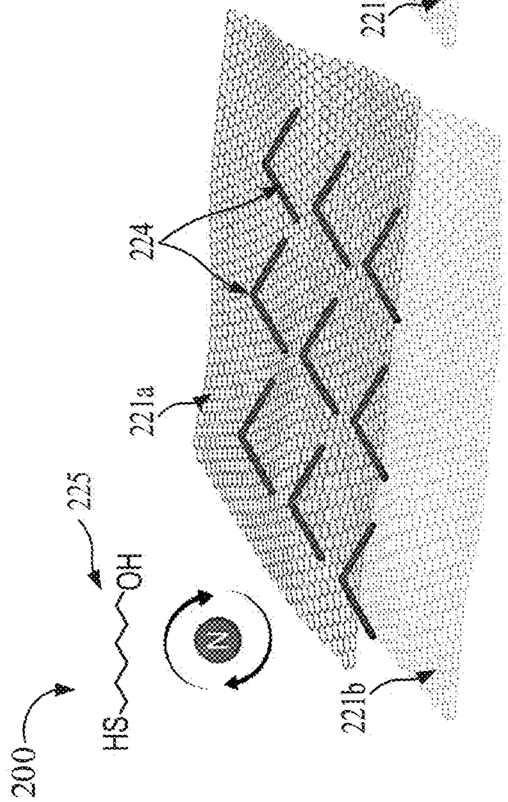

FIG. 3F shows a fourth processing step following the exposure of the Au working electrode 221 to a high purity $N_2$ described above. More specifically, FIG. 3F schematically depicts that the Au working electrode 221 with Nitrogen electrostatically bound to the thiol groups of the anchor layer 230 (not shown in FIG. 3F for simplicity) can be treated with a site-blocking reagent 225 such as 6-Mercapto-1 Hexanol to passivate nano ridges 224 which are not covalently bound to thiol groups of the anchor layer 230, and thus are free to bind and/or conjugate unwanted species on the Au working electrode 221. The site-blocking reagent 225 can be a linear hydrocarbon molecule that may exhibit chirality and may include a thiol functional disposed at a one end of the molecule and a hydroxyl group bound to the other end of the molecule. The site-blocking reagent 225 can cause desorption of adsorbed Nitrogen from the nano ridges 224 and/or any other Au surface sites which are not covalently bound to thiol groups, as schematically shown in FIG. 3F. The thiol groups present on the site-blocking reagent 225 (e.g., 6-Mercapto-1 Hexanol molecule) can bind to those free nano ridges 224 and/or the free Au surface sites on the Au working electrode 221 according to a reaction pathway similar to that of the thiol groups of the anchor layer 130 and 230 described above. The reaction of the free nano ridges 224 and/or free Au surface sites on the Au working electrode 221 with a site blocking reagent 225 such as 6-Mercapto-1 Hexanol produces strong S—Au covalent bonds that can immobilize the 1-Mercapto-1 Hexanol molecule to the surface of the Au working electrode 221 and provide hydroxyl functional groups attached to the Au working electrode 221 and/or nano ridges 224. In some embodiments, the site-blocking reagent 225 can be exposed to the Au working electrode 221 by disposing a small volume of a liquid solution comprising the site-blocking reagent 225, and incubating the liquid solution for a period of time to allow the site-blocking reagent 225 molecules to react with the free nano ridges 224 and any other free or loosely bound Au surface sites on the Au working electrode 221, blocking those sites from binding and/or conjugating unwanted species and/or contaminants. Exposure of the Au working electrode 221 to a site-blocking reagent 225 such as 6-Mercapto-1 Hexanol facilitates isolating the thiol-immobilized anchor layer 230 from reactive sites present on the Au working electrode 221 and/or nano ridges 224 which could conjugate unwanted species (e.g., preventing non-specific binding to the Au working electrode surface).

Figure 3G:
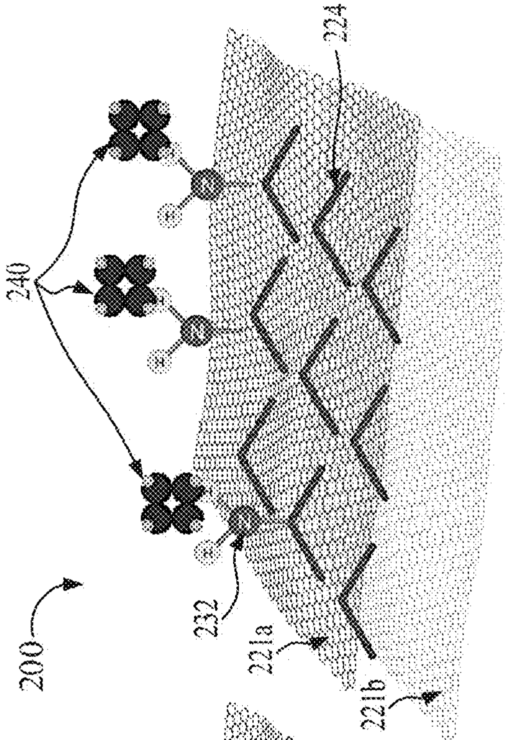

FIG. 3G schematically shows a fifth processing step after the nano ridges 224 on the activated outer surface layer **221*a* of the Au working electrode 221 are covalently bound to the anchor layer 230 via thiol functional groups, and a site blocking reagent 225 has been used to passivate active sites on the Au working electrode 221 not covalently bound to the anchor layer 230, as described above. FIG. 3G shows the Au working electrode 221 can be exposed to a solution comprising a linker 240 with the purpose of binding, conjugating, attaching, and/or tethering the linker 240 to the anchor layer 230 (not shown) of the biosensor 200. The linker 240 can include biotin-binding proteins such as streptavidin, which can react with the surface carboxylic functional groups of the anchor layer 230 via primary amine groups present on the linker 240. In some embodiments, the surface carboxylic functional groups of the anchor layer 230 can react with the primary amine groups of the linker 240 with the aid of a carbodiimide additive such as 1-Ethyl-3-(3-dimethylaminopropyl) carbodiimide (EDC), and/or N-hydroxysuccinimide (NHS). The EDC/NHS additives can be added the solution comprising the linker 240 to facilitate the formation of an unstable intermediate species between the surface carboxylic functional groups and the EDC/NHS reagents, which can then react with the primary amines of the linker 240 to produce stable amide bonds 232. The amide bonds 232 can bind, conjugate, attach, and/or tether the linker 240 to the surface of the Au working electrode and/or the nano ridges 224, as shown in FIG. 3G. The reaction between the primary amines present in the linker 240 and the surface carboxylic functional groups of the anchor layer 230 proceeds as described above with reference to the reaction between the linker 140 and the anchor layer 130 in FIG. 2. In some embodiments, the solution comprising the linker 240 can also include one or more suitable buffer solution. The buffer solution can be configured to maintain a stable and/or controlled pH during the reaction between primary amines of the linker 240 and the carboxylic groups of the anchor layer 230. In some embodiments, the buffer solution can include one or more aqueous buffers solutions such as PBS, HEPES, TRIS, PIPES, MES and the like. For example, in some embodiments an EDC/NHS solution can be prepared by dissolving 11.5 mg of NHS in 500 μL of MEMS buffer pH 4.5, and subsequently adding 250 μL of an EDC solution prepared by mixing 21.6 mg of EDC with 500 μL of deionized (DI) water. The resulting EDC/NHS solution can be vortexed for 30 seconds to facilitate adequate mixing, and then 10 μl of the EDC/NSH solution can be added to the biosensor 200 to assist the reaction of the surface carboxylic functional groups of the anchor layer 230 and the primary amine groups of the linker 240, according to the reaction shown in FIG. 2B. In some embodiments the solution can include a PBS buffer configured to maintain a neutral pH (e.g., pH=7.0) during the EDC/NHS mediated reaction between the linker 240 and the anchor layer 230**.

Figure 3H:
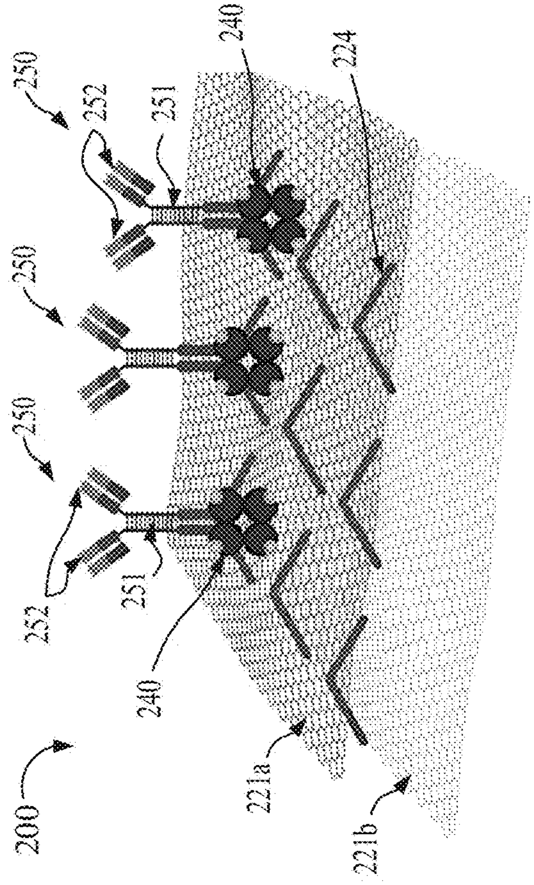

FIG. 3H schematically shows a sixth processing step after the nano ridges 224 on the activated outer surface **221*a* of the Au working electrode 221 are bound to the linker 240, as described above with reference to FIG. 3G. More specifically, FIG. 3H shows the Au working electrode 221 can be exposed to a solution comprising a recognition component 250. As described above with reference to the recognition component 150 in FIG. 1, the recognition component 250 can include one or more affinity molecules and/or reagents such as antibodies (Ab) that can recognize toxins, antigens and/or other foreign substances associated with unique target species such as fungi, parasites, pathogenic bacteria and/or viruses. The recognition component 250 can include biotinylated antibodies having biotin molecules configured to bind to the streptavidin molecules of the linker 240, thus binding, conjugating, attaching, and/or tethering the recognition component 250 to the Au working electrode 221 and nano ridges 221, as shown in FIG. 3H. For example, in some embodiments, the recognition component 250 can include an antibody having biotin molecules bound to a C-terminus of the antibody, configured to bind to the streptavidin molecules of the linker 240** via protein-binding interactions.

In some embodiments, the biotinylated antibodies of the recognition component 250 can be bound to the linker 240 while running a negative current and/or a voltage through the Au working electrode 221 for a predetermined amount of time. In such embodiments, the Au working electrode 221 can be first electrically coupled to an electrochemical testing unit (e.g., via a cartridge) to send a negative current from the electrochemical testing unit to the electrode 220, and then exposed to a solution comprising the recognition component 250. The negative current flowing through the Au working electrode 221 can substantially impact the orientation of the bound antibodies on the streptavidin molecules of the linker 240, resulting in a high percentage of antibodies bound to the linker 240 according to an orientation in which the Fc 251 region is directly attached and/or conjugated to the linker 240 and the Fab region 252 points away from the biosensor 200 (e.g., tail-on orientation), as shown in FIG. 3G. For example, in some embodiments, a recognition component 250 can include a biotinylated antibody which can be bound to the linker 240 by exposing the surface of the Au working electrode to a solution containing the biotinylated antibody and simultaneously running a negative voltage of −0.2 V for a period of time of about 6 seconds. The voltage applied to the electrode 220 can impact the orientation of the bound antibodies on the streptavidin molecules of the linker 240, resulting in a substantially high percentage of antibodies bound to the linker 240 according to an orientation in which the Fc region 251 is directly attached and/or conjugated to the linker 240 and the Fab region (252) points away from the biosensor 200 (e.g., tail-on orientation). In some embodiments, the voltage sent from the electrochemical testing unit to the electrode 220 can be at least about −0.2 V, at least about −0.15 V, at least about −0.10 V, at least about −0.05 V, at least about 0.05 V, at least about 0.10 V, at least about 0.15 V, at least about 0.2 V, inclusive of all values and ranges therebetween. In some embodiments, the voltage sent from the electrochemical testing unit to the electrode 220 can be no more than about 0.2V, no more than about 0.16 V, no more than about 0.12 V, no more than about 0.08 V, no more than about 0.04 V, no more than about −0.04 V, no more than about −0.08 V, no more than about −0.12V, no more than about −0.16 V, no more than about −0.20 V, inclusive of all values and ranges therebetween. Combinations of the above referenced voltage sent from the electrochemical testing unit to the electrode 220 are also possible (e.g., a voltage of at least about −0.2V to no more than about 0.15V, at least about −0.1V to no more than 0.05V).

Figure 5:
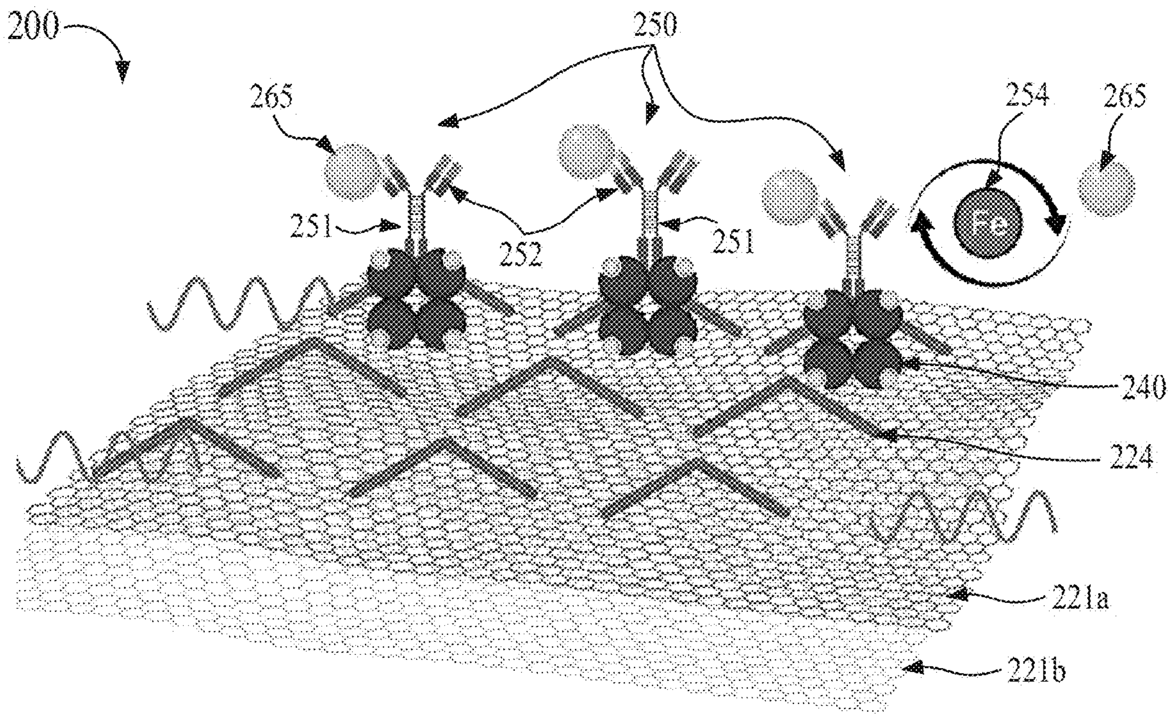
FIG. 5 is a schematic illustration of a method of using the electrochemical biosensor of FIG. 3H to sense and/or detect a target species in a biological sample.

FIG. 5 schematically illustrates a method of using the electrochemical biosensor 200 to conduct the electrochemical analysis of biological samples comprising one or more target species. As described above, the biosensor 200 includes a working electrode 221 with an activated outer surface 221*a* and nano ridges 224, a linker 240 bound via an anchor layer (not shown) to the nano ridges 224, and a recognition component 250 which can include antibodies (Ab) bound and/or conjugated to the linker 240 and oriented on the biosensor 200 such that the Fc region 251 of the antibodies (Ab) is directly attached to the linker 240 and the Fab region 252 points away from the biosensor 200 (e.g., tail—on orientation). In use, the biosensor 200 can be coupled to a sample processing unit and to an electrochemical testing unit via a cartridge (not shown) to expose the biosensor 200 to a biological sample and conduct electrochemical analysis of the biological sample comprising one or more target species 265, as described above with reference to the biosensor 100 and the cartridge 172. The biological sample can be a saliva sample, a urine sample, a blood sample, a plasma sample, a serum sample, or the like, comprising a target species 265 as shown in FIG. 5.

The target species 265 can be an antigen, toxin, and/or other foreign substance associated with fungi, parasites, pathogenic bacteria and/or viruses, which can be selectively bound and/or conjugated by the recognition component 250. For example, in some embodiments the target species 265 can be an antigen associated with pathogens such as norovirus, SARS-CoV-2 and the like. The biological samples can be mixed with a solution containing a reporter molecule 254 to produce a biological sample mixture. In some embodiments, the biological sample mixture can have a concentration of reporter molecule equal to the concentration of recognition components disposed on the surface of the biosensor 200. For example, in some embodiments the concentration of reporter molecule can be at least about 0.1 mM, at least about 0.5 mM, at least about 1 mM, at least about 2 mM, at least about 2.5 mM, at least about 3 mM, at least about 4 mM, at least about 5 mM, at least about 10 mM, inclusive of all values and ranges therebetween. The biological sample mixture can then be placed in physical contact with the electrochemical biosensor 200 to conduct its electrochemical analysis. In some embodiments, the biological sample can be mixed with the solution containing the reporter molecule 254 in a sample processing unit via microfluidic channels, as described above with reference to the sample processing unit 100. In some embodiments, the biological sample can be mixed with the solution containing the reporter molecule 254 by disposing a volume of the solution containing the reporter molecule 254 with pipette, a syringe, and/or the like into an interior volume, compartment, and/or chamber of a sample processing unit storing and/or containing the biological sample.

The reporter molecule 254 can include a redox pair that exhibits a reversible electrode reaction substantially free from unwanted secondary reactions that can be measured, and/or monitored via standard electrochemical characterization techniques and/or diagnostic tests such as cyclic voltammetry, pulse voltammetry, square wave voltammetry, and/or strip voltammetry, as further described herein. In some embodiments, the reporter molecule 254 can include a ferrocyanide/ferricyanide pair (e.g., $[Fe(CN)_6]^{3-/4-}$) which exhibit a one electrode reversible electrochemical redox reaction substantially free from unwanted side reactions, and that can be measured, and/or monitored via cyclic voltammetry, pulse voltammetry, square wave voltammetry, and the like. In some embodiments, the reporter molecule 254 can include Ferrocene and/or methylthioninium chloride (Methylene Blue).

The biological sample comprising the target species 265 and the reporter molecule 254 can be directed and/or disposed in physical contact with the biosensor 200 to initiate its electrochemical analysis. In some embodiments, the biological sample comprising the target species 265 and the reporter molecule 254 can be directed and/or disposed in physical contact with the biosensor 200 within a sample processing unit, as described above.

The reporter molecule 254 can electrostatically oppose all the species present in the biological sample including the target species 265, proteins, antigens, toxins, and/or other analytes. Electrical excitation signals such as a current and/or a voltage can be generated by the electrochemical testing unit and sent and/or applied to the Au working electrode 221 to initiate the electrochemical analysis of the biological sample comprising the target species or target species 265 and the reporter molecule 254. Electrical excitation signals sent and/or applied the Au working electrode 221 such as a voltage and/or potential can initiate the reversible electrochemical reaction of the reporter molecule 254, cause the reporter molecule 254 to electrostatically bind with the species present in the biological sample including the target species 265, proteins, antigens, toxins, and/or other analytes, and induce an electrical current on the Au working electrode 221 which can be detected, measured and monitored with the electrochemical testing unit. Without being bound by any particular theory, it is believed that under these conditions, the Au working electrode 221 can exhibit localized surface plasmon resonance among the nanostructures (e.g., nano ridges 224 and/or grooves 226) causing electrons to jump between nano ridges 224 and/or grooves 226, thereby increasing their electromagnetic field, and attracting and/or pulling the analytes present in the biological sample to the Au working electrode surface, forming an affinity cloud in the close vicinity of the surface of the working electrode 221 (e.g., at distance of about 30 nm from the surface of the working electrode 221). The strong affinity of the recognition component 250 towards the target species 265 favors the selective binding of the target species 265 to the recognition component 250 over electrostatic binding with the reporter molecule 254. Other non-target species present on the biological sample remain electrostatically bound to the reporter molecule 254 and do not bind and/or conjugate to the recognition component 250. Said in other words, only the target species 265 can overcome the electrostatic binding interaction with the reporter molecule 254 and bind and/or conjugate to the antibodies of the recognition component 250 at to the Fab region 252, as shown in FIG. 5, while the other species present in the biological sample remain electrostatically bound to the reporter molecule 254. In this way, the reporter molecule 254 can effectively improve the selectivity of the recognition component 250 towards the target species 265 by preventing binding of non-target species to the recognition component 250 (e.g., avoiding loosely bound species). The improved sensitivity of the recognition component 250 towards the target species 265 can translate in higher sensitivity and lower limit of detection (LLD) of the biosensor 200. For example, in some embodiments, the biosensor 200 can achieve LLD which are about 70 to 80 times lower than alternative biosensors.

As described above, the electrical excitation signals sent and/or applied the working electrode 221 such as a voltage and/or potential initiate the reversible electrochemical reaction of the reporter molecule 254, causing the reporter molecule 254 to electrostatically bind with the species present in the biological sample and produce a response signal (e.g., a response current) that can be detected, measured and monitored with the electrochemical testing unit. This response signal and/or current is proportional to the concentration of species that bind electrostatically to the reporter molecule 254. Since the target species 265 can bind selectively to the antibodies of the recognition component 250, they do not contribute to the electrical current detected, measured and monitored with the electrochemical testing unit. As a result, the binding of the target species 265 to the recognition component 250 reduces the total current measured by the electrochemical testing unit. In this way, the current measured by the electrochemical testing unit can be used as a transducer element to determine the concentration of the target species 265. Electrochemical analysis of samples having a predetermined concentration of reporter molecules 254 will generate a current that is inversely proportional to the concentration of target species 265. For example, biological samples having a predetermined concentration of the reporter molecule 254, and which do not include the target species 265 can produce a first electrical current during electrochemical testing of the biological sample. Biological samples having the predetermined concentration reporter molecule 254, and which do include the target species 265 can produce a second electrical current during electrochemical testing of the biological sample, with the second electrical current being smaller than the first electrical current. The difference between the first electrical current and the second electrical current is proportional to the concentration of target species 254 present in the biological sample, as further described herein.

The electrical signals generated by the electrochemical testing unit and sent and/or applied to the working electrode 221 during the electrothermal testing of a biological sample, as described above, can correspond to any suitable voltametric method such as a linear sweep, cyclic voltammetry, pulse voltammetry, square wave voltammetry, differential pulse voltammetry, stripping voltammetry or the like. For example, in some embodiments, the electrical signals generated by the electrochemical testing unit and sent and/or applied to the working electrode 221 during the electrothermal testing of a biological sample can include a Differential Pulse Voltammetry (DPV) signal. Differential Pulse Voltammetry is a controlled-potential method in which a series of regular voltage pulses are superimposed on a linearly increased potential sweep. Current is measured immediately before each voltage pulse and at the end of the pulse, and the difference between them is recorded as a function of the potential.

Figure 6B:
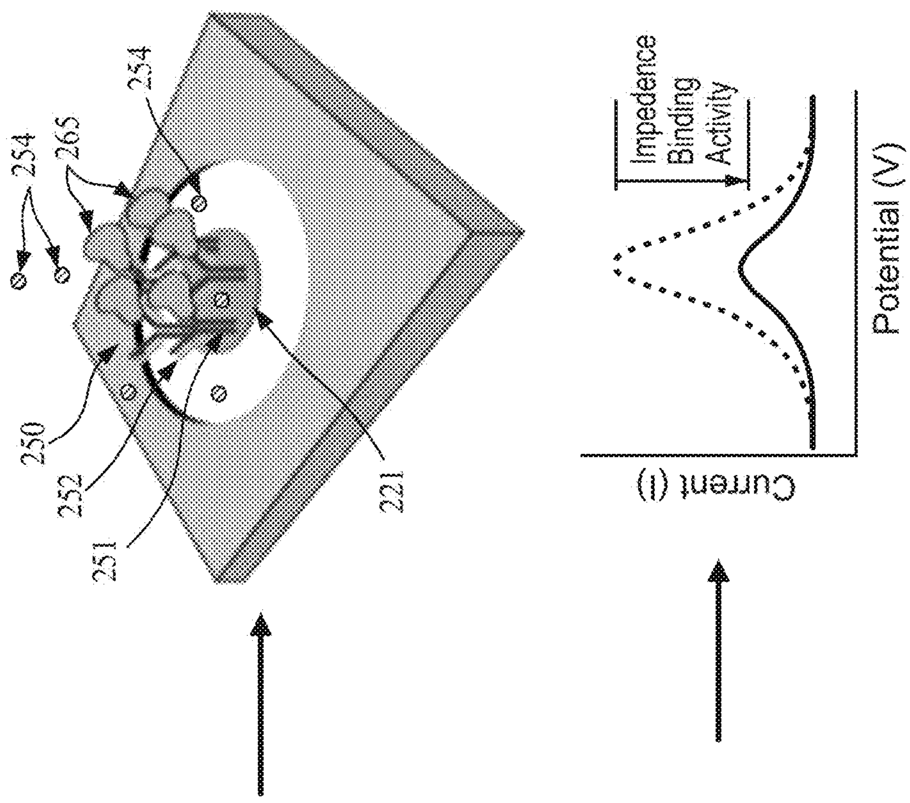
FIGS. 6A and 6B are schematic illustrations of a differential pulse voltammograms recorded during detection and quantification of a target species present on a biological sample with the electrochemical biosensor of FIG. 3H.
Figure 6A:
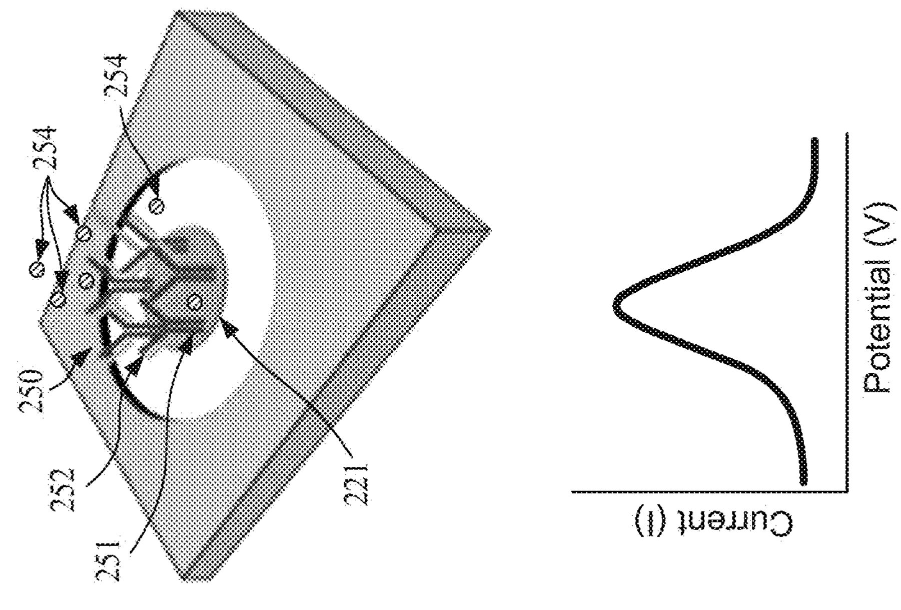

FIGS. 6A-6B show a schematic illustration of the biosensor 200 and DPV data recorded during electrochemical analysis of a first biological sample that does not include a target species 265 (see FIG. 6A), and a second biological sample that does include a target species 265 (see FIG. 6B). The biosensor 200 includes a working electrode 221 coupled to a recognition component 250 via a linker and anchor layer (not shown). The recognition component 250 can include antibodies (Ab) oriented on the biosensor 200 such that a Fab region 252 of the antibodies points away from the biosensor 200 (e.g., tail—on orientation) as described in detail above. FIG. 6A shows a DPV plot displaying the response of the biosensor 200 during electrochemical analysis of the first biological sample (e.g., the biological sample which does not include target species 265). The first biological sample comprises a predetermined concentration of a reporter molecule 254. The reporter molecule 254 can be similar to and/or the same as the reporter molecule(s) described above with reference to the biosensor 100. Electrical excitation signals sent and/or applied the Au working electrode 221 such as a voltage and/or potential can initiate the reversible electrochemical reaction of the reporter molecule 254 and cause the reporter molecule 254 to electrostatically bind with the species present in the biological sample generating a current response as shown in the DPV plot in FIG. 6A.

FIG. 6B shows a DPV displaying the response of the biosensor 200 during electrochemical analysis testing of the second biological sample (e.g., the biological sample that does include a target species 265). The second biological sample comprising the same predetermined concentration of the reporter molecule 254 of FIG. 6A. The DPV of FIG. 5B shows the biosensor 200 generated a smaller current response as compared to the current response of FIG. 6A. The difference in the current response between the voltammograms of FIG. 6A and FIG. 6B is proportional to the concentration of the analyte (e.g., target species 265) present in the biological samples.

The DPV response shown in FIG. 6A can be recorded and used as a control sample response. For example, in some embodiments, a number of biological samples such as saliva samples can be collected from a population. The biological samples can include a first portion of samples collected from individuals which do not carry and/or have the pathogen, and thus their saliva does not include the target species 265 (e.g., a control sample). The biosensor 200 can be used to test the first portion of biological samples to characterize the typical response of the biosensor 200 during electrochemical testing of saliva samples obtained from individuals deemed to be pathogen/free. An individual can be deemed to be pathogen free by testing a sample of their saliva using an alternative analytical method such as an ELISA test. In some embodiments, the DPV responses obtained from the first portion of biological samples can be fed to a machine learning algorithm to facilitate identification of a pathogen free response. The biological samples can also include a second portion of samples collected from individuals which either (1) do carry the pathogen associated to the target species 265 as determined by alternative test such as an ELISA test, or (2) can be spiked with a known concentration the target species 265. The biosensor 200 can then be used to test the second portion of biological samples to characterize the responses of the biosensor 200 during electrochemical testing of saliva samples obtained from individuals deemed to have the pathogen and the associated target species 265, or biological samples spiked with known concentrations of the target species 265.

Figure 7A:
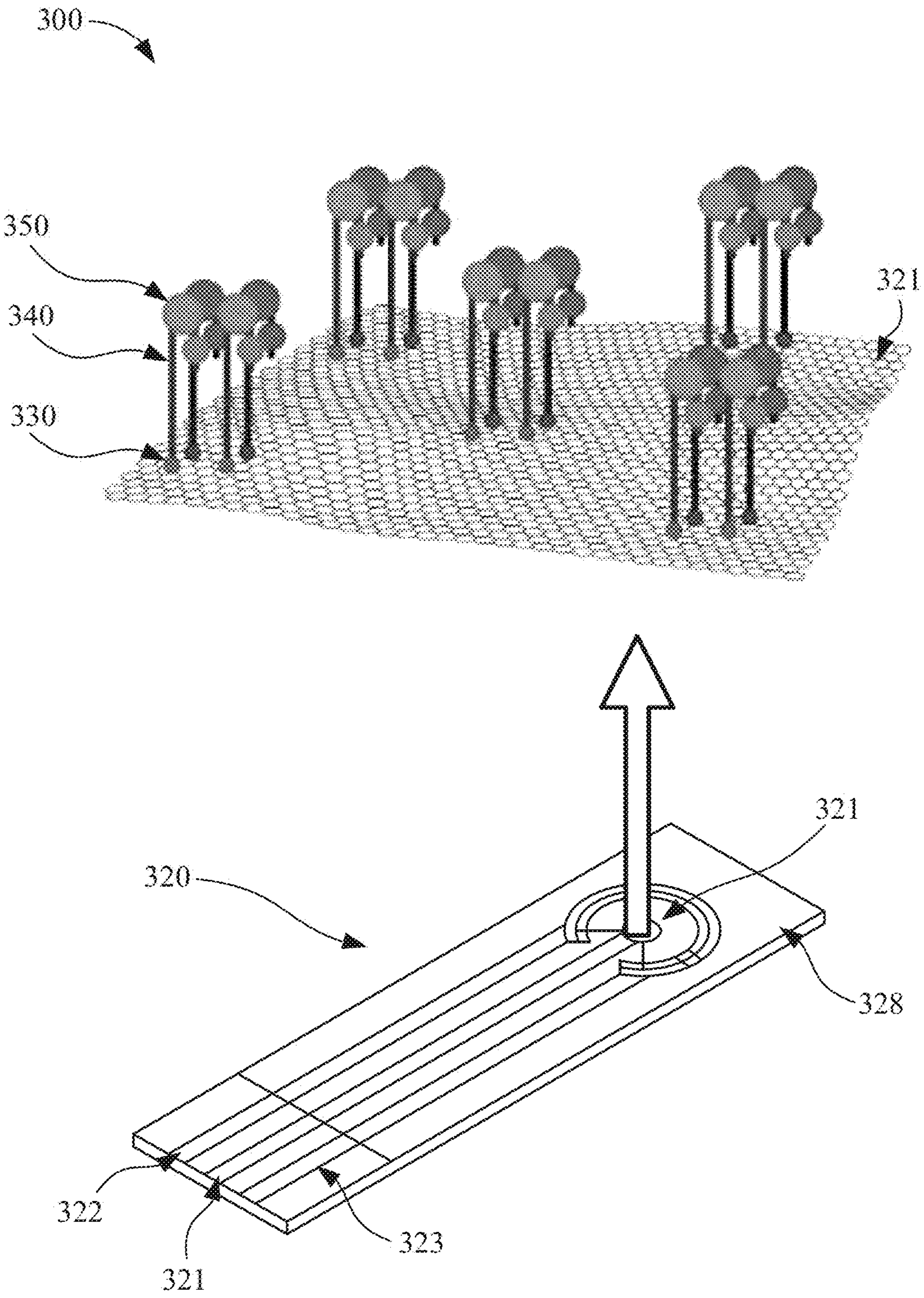
FIG. 7A is a schematic illustration of an electrochemical biosensor according to an embodiment.

FIG. 7A shows a schematic illustration of an electrochemical biosensor 300 according to an embodiment. The electrochemical biosensor 300, which can also be referred to as the biosensor 300, can be similar to and/or substantially the same as one or more portions (and/or combination of portions) of the biosensor 100 and 200 described above with reference to FIGS. 1-6. More specifically, the biosensor 300 can be substantially similar in at least form and/or function to the biosensor 100 and the biosensor 200 described in detail above. Thus, portions and/or components of the biosensor 200 may not be described in further detail herein. The biosensor 300 includes an electrode 320 configured to send and receive electrical signals which can be associated with electrochemical reactions. The electrode 320 can be a standard screen-printed electrode strip comprising a working electrode 321, a counter electrode 322, and a reference electrode 323 disposed on a plastic and/or ceramic support 328. In some embodiments, the working electrode 321, the counter electrode 322, and the reference electrode 323 can be made of any suitable material including gold (Au), platinum (Pt), silver (Ag), carbon (C), carbon nanotubes (CNT), and the like. For example, in some embodiments, the electrode 320 can include a gold (Au) working electrode 321, a carbon (C) counter electrode 322, and a (Pt) reference electrode 323 disposed and/or arranged according to a three-electrode configuration.

In some implementations, the working electrode 321 can be fabricated according to a procedure similar to the fabrication procedures described above with reference to the biosensor 200. For example, in some embodiments the working electrode 321 can be treated by exposing the working electrode 321 to strong oxidizing agents such as $H_2O_2$, etching solutions containing reagents such as potassium iodide (KI) and iodine (12), strong acid such as hydrochloric acid (HCl), an etching treatment with a laser gun, and/or sanding procedures with abrasive materials. In such implementations, the counter electrode 322 and the reference electrode 323 can be coated and/or masked with a protective layer to prevent altering the structure and/or composition of the counter electrode 322 and the reference electrode 323, following procedures well known in the art.

The biosensor 300 includes an anchor layer 330 that comprises bifunctional molecules and/or species having a first chemical functionality consisting of sulfur-containing groups that react chemically (via chemisorption) with the working electrode 321 creating strong metal-sulfur bonds (M-S bonds) on the surface of the working electrode 321, and a second chemical functionality comprising reactive functional groups such as carboxylic acid, alcohol, aldehyde, ketone, amine, and/or epoxide that can bind, attach, and or tether other components of the biosensor 300 to the anchor layer 330 via chemical reactions that produce strong covalent bonds. The anchor layer 330 can be immobilized on the electrode 321 via thiol functional groups, similar to the anchor layer 130 and 230 described above. The anchor layer 330 can also be coupled to a linker 340 via EDC/NHS reactions, as described above with reference to FIG. 2. The linker 340 can include biotin binding proteins such as streptavidin, avidin, neutravidin, and/or captavidin, which can be coupled to a recognition component 350 via biotinylated affinity molecules. In some embodiments, the biosensor 300 fabrication procedure can be configured to generate clusters, bundles, groups, and/or agglomerates of recognition components 350 surrounded by passivated regions in which the working electrode 321 has not been coupled to an anchor layer 330, linker 340, and/or recognition component 350, as shown in FIG. 7A.

Figure 7B:
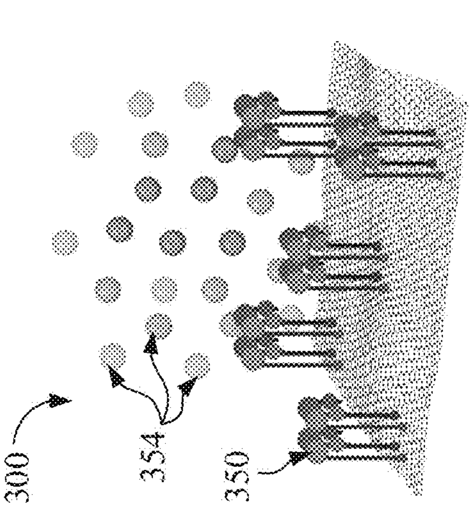
FIGS. 7B-7E schematic illustrate the use of the biosensor shown in FIG. 7A for the electrochemical analysis of biological samples comprising one or more target species, according to an embodiment.

In use, the biosensor 300 can be coupled to a sample processing unit (not shown) and to an electrochemical testing unit via a cartridge (not shown) to expose the biosensor 300 to a biological sample and conduct electrochemical analysis of the biological sample comprising one or more target species. The biological sample can be a saliva sample, a urine sample, a blood sample, a plasma sample, a serum sample, or the like. In some embodiments, the target species can be an antigen, toxin, and/or other foreign substance associated with fungi, parasites, pathogenic bacteria and/or viruses, which can be selectively bound and/or conjugated by the recognition component 350. The biological samples can be mixed and/or diluted with a solution containing a reporter molecule 354 prior to conducting its electrochemical analysis with the biosensor 300. FIG. 7B shows a schematic representation of the biosensor 300 exposed to a biological sample comprising a reporter molecule 354 at a predetermined concentration. The reporter molecule 354 can include a redox pair such as a ferrocyanide/ferricyanide pair (e.g., $[Fe(CN)_6]^{3-/4-}$) which exhibit a one electrode reversible electrochemical redox reaction substantially free from unwanted side reactions, and that can be measured, and/or monitored via cyclic voltammetry, pulse voltammetry, square wave voltammetry, and the like using the electrode 320.

Figure 7C:
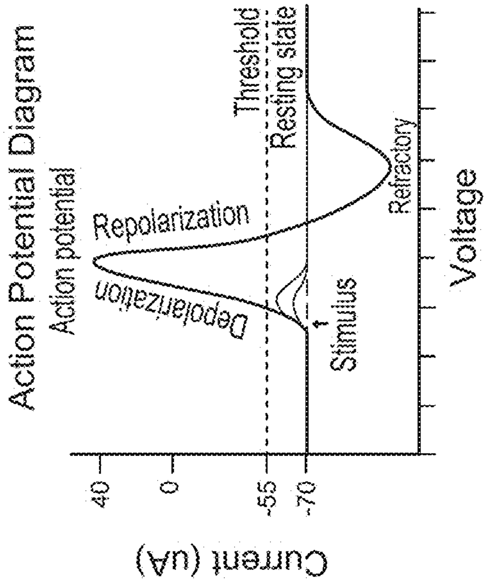
Figure 7D:
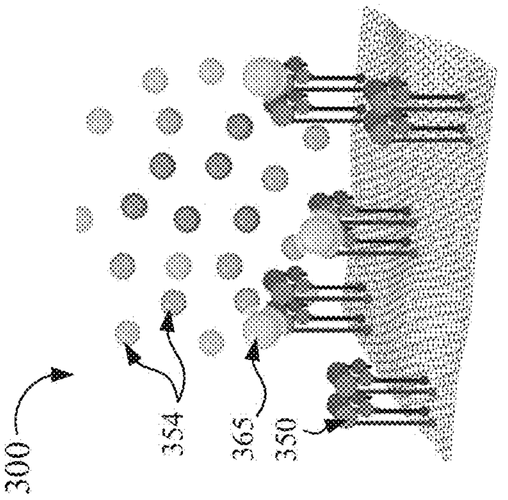

Electrical signals such as DPV can be generated by the electrochemical testing unit and sent and/or applied to the working electrode 321 to initiate the electrochemical analysis of the biological sample comprising the reporter molecule 354 and no target species, as described above with reference to FIG. 6A. The electrical signals sent and/or applied the working electrode 321 such as a voltage and/or potential can initiate the reversible electrochemical reaction of the reporter molecule 354, cause the reporter molecule 354 to electrostatically bind with species present in the biological sample, and induce an electrical current on the working electrode 321 which can be detected, measured, and/or monitored with the electrochemical testing unit. The measured electrical current can be plotted as a function voltage, as shown in FIG. 7C. This Current-Voltage plot can then be used as a baseline and/or reference response to compare electrical current responses measured and/or obtained with biological samples that include the reporter molecule 354 at the same predetermined concentration, and a target species 365. FIG. 7D shows a schematic illustration of such a biological sample including the reporter molecule 354 at the predetermined concentration, and a target species 365. Electrical signals such as DPV can be generated by the electrochemical testing unit and sent and/or applied to the working electrode 321 to initiate the electrochemical analysis of the biological sample comprising the target species 365 and the reporter molecule 354. The electrical signals sent and/or applied the working electrode 321 such as a voltage and/or potential can initiate the reversible electrochemical reaction of the reporter molecule 354 and cause the reporter molecule 354 to electrostatically bind with species present in the biological sample. The target species 365, which may include proteins, antigens, toxins, and/or other analytes, will not bind electrostatically to the reporter molecule 354 and instead will bind preferentially to the recognition component 350 as shown in FIG. 7D. Since the target species 365 does not bind electrostatically to the reporter molecule 354, it does not contribute to the electrical current measured by the electrochemical testing unit. Consequently, the electrical current responses measured for biological samples containing an unknown concentration of the target species 365 can be compared to the reference and/or baseline current response described above to determine the concentration of the target species 365. Without being bound by any particular theory, it is believed that under these conditions, the working electrode 321 can exhibit localized surface plasmon resonance among the nanostructures (e.g., nano ridges 224 and/or grooves 226) causing electrons to jump between nano ridges (not shown) increasing their electromagnetic field, and attracting and/or pulling the analytes present in the biological sample to the surface of the clusters of recognition component 350, forming an affinity cloud in the close vicinity of the working electrode 321 (e.g., at distance of about 30 nm from the surface of the working electrode 321). The strong affinity of the recognition component 350 towards the target species 365 favors the selective binding of the target species 365 to the clusters of recognition component 350 over electrostatic binding with the reporter molecule 354, as shown in FIG. 7D. Other non-target species present on the biological sample remain electrostatically bound to the reporter molecule 354 and do not bind and/or conjugate to the recognition component 350.

Figure 7E:
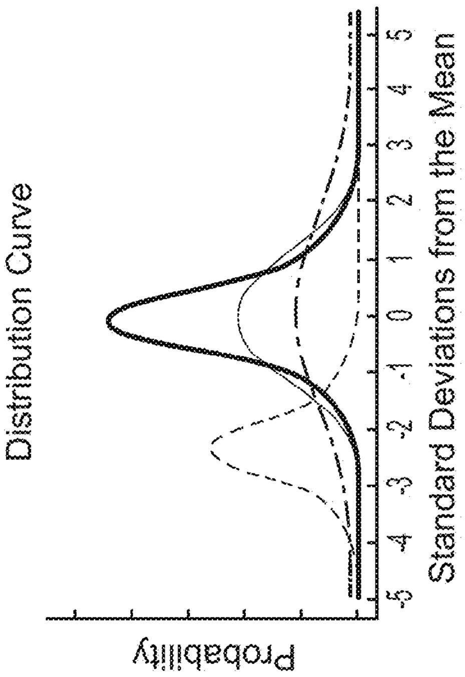

As described above with reference to FIGS. 5 and 6 the current measured by the DPV can be used as the biosensor transducer element to determine the concentration of the target species 365. Electrochemical analysis of a sample having a predetermined concentration of reporter molecules 354 will generate a current that is inversely proportional to the concentration of target species 365. In some embodiments, the DPV responses obtained during electrochemical analysis of biological samples with the biosensor 300 can be used to create a standard curve, as shown in FIG. 7E, which can be validated with for example, other analytical methods such as enzyme-linked immunosorbent assay (ELISA), similar to and/or as described above with reference to FIG. 6.

Figure 8A:
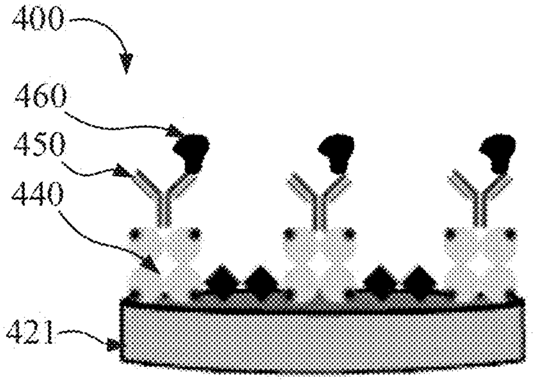
FIGS. 8A and 8B are schematic illustrations of an electrochemical biosensor according to an embodiment.
Figure 8B:
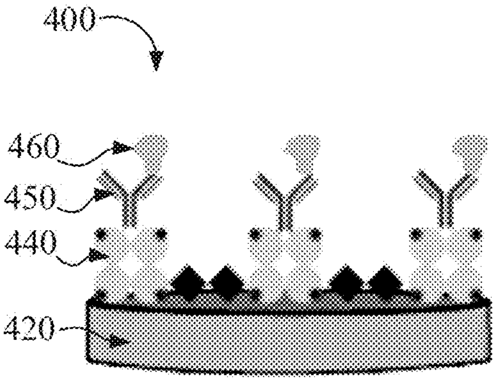

FIGS. 8A and 8B show schematic illustrations of an electrochemical biosensor 400 according to an embodiment. The electrochemical biosensor 400, which can also be referred to as the biosensor 400, can be similar to and/or substantially the same as one or more portions (and/or combination of portions) of the biosensor 100, 200, and 300 described above with reference to FIGS. 1-7. More specifically, the biosensor 400 can be substantially similar in at least form and/or function to the biosensor 100, 200 and 300 described in detail above. Thus, portions and/or components of the biosensor 400 may not be described in further detail herein. The biosensor 400 includes a working electrode 421, having an anchor layer (not shown) configured to react chemically (via chemisorption) with the working electrode 421 creating strong metal-sulfur bonds (M-S bonds), and comprising reactive functional groups that can bind a linker 440 via covalent bonds. The linker 440 can include biotin binding proteins such as streptavidin, avidin, neutravidin, and/or captavidin, which can be coupled to a recognition component 450 via biotinylated affinity molecules. The biosensor 400 also includes a visualization component 460 coupled and/or conjugated to the recognition component 450, as shown in FIGS. 8A and 8B.

Figure 8C:
FIGS. 8C and 8D are black and white fluorescence micrographs of the electrochemical biosensor of FIGS. 8A and 8B, respectively.
Figure 8D:
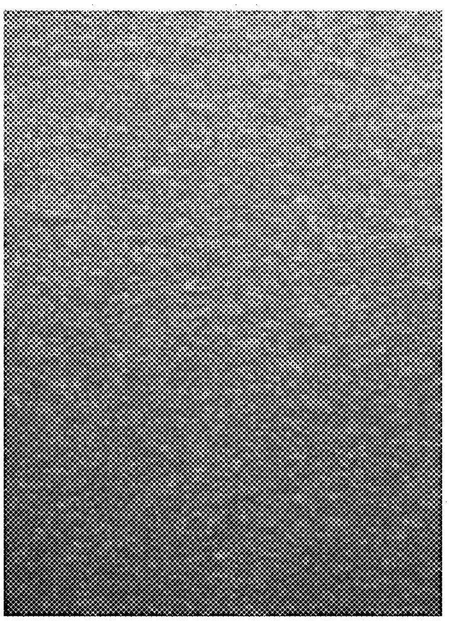

The visualization component 460 can include one or more optical elements such as a fluorescent dye, protein, and/or probe configured to absorb light and emit, in response to the absorbed light, a fluorescence signal which can be detected and/or imaged by any suitable detector such as a CCD detector, EM-CCD detector, and/or a CMOS detector. In some embodiments the visualization component 460 be tagged and/or conjugated to the recognition component 450 and can be used to image the biosensor 400 by standard microscopy techniques, facilitating the characterization of the recognition component 450 on the biosensor 400. For example, in some embodiments the visualization component 460 can include Alexa Fluor fluorescent probes tagged to antibodies of the recognition component 450 and configured to be illuminated with a suitable wavelength light source to induce a fluoresce emission response from the Alexa Fluor fluorescent probes that can be detected and imaged by a detector of a standard Fluorescence microscope, as shown in FIG. 8C. The micrographs of the visualization component 460 recorded by the detector can be used to characterize the distribution, orientation, surface density, and/or coverage of the recognition component 450 on the biosensor 400. In other embodiments the visualization component 460 can include FITC fluorescent probes tagged antibodies of the recognition component 450 and configured to be illuminated with a suitable wavelength light source to induce a fluoresce emission response from the FITC fluorescent probes that can be detected and imaged by a detector of a standard Fluorescence microscope, as shown in FIG. 8D. The micrographs of the visualization component 460 recorded by the detector can be used to characterize the distribution, orientation, surface density, and/or coverage of the recognition component 450 on the biosensor 400.

In some embodiments, the visualization component 460 can include a single type of fluorescent dye, protein, and/or probe configured to be coupled to a component of the biosensor 400 to absorb light and emit a fluorescence response at a suitable range of wavelengths, facilitating the characterization of the components of the biosensor 400 such as, for example, the anchor layer 430, the linker 440, and/or the recognition component 450. For example, in some embodiments the visualization component 460 can include a fluorescent dyes, protein, and/or probe including Pacific Blue, Alexa Fluor 488, Alexa Fluor 546, Alexa Fluor 633, FITC, Rhodamine 110, Rhodamine 123, Cy2, Cy5, DayLight 350, DayLight 405, Coumarin, DAPI, Marina Blue, CFP, eCFP, BOPRO-1, GFP, DTAF, CFDA, FITC, Acridine orange, and the like.

In some embodiments, the visualization component 460 can include multiple types of fluorescent dyes, proteins, and/or probes configured to be coupled to specific components of the biosensor 400 to absorb light and emit fluorescence responses at different wavelengths, facilitating the simultaneous characterization of one or more components of the biosensor 400. In such embodiments, the visualization component 460 can include fluorescent dyes, proteins, and/or probes selected due to their non-overlapping excitation wavelengths and/or emission wavelengths. For example, in some embodiments the visualization component 460 can include Alexa 488 fluorescence probes tagged to a first portion of the recognition component 450 which includes a first type of antibody, and Alexa 555 probes tagged to a second portion of the recognition component 450 which includes a second type of antibody. Exposure of the visualization component 460 to a light source having an excitation wavelength including 493 nm (e.g., the excitation peak wavelength for Alexa 488) results in absorption of light by the Alexa 488 fluorescence probes tagged to the first portion of the recognition component 450 and emission of fluorescence at a maximum emission wavelength of 519 nm. Similarly, exposure of the visualization component 460 to a light source having an excitation wavelength including 553 nm (e.g., the excitation peak wavelength for Alexa 555) results in absorption of light by the Alexa 555 fluorescence probes tagged to the second portion of the recognition component 450 and emission of fluorescence at a maximum emission wavelength of 568 nm. The fluorescence emission of the Alexa 488 and the Alexa 555 probes can be capture by suitable detectors and can be imaged with the aid of standard microscopy techniques to characterize the distribution, orientation, surface density, and/or coverage of the first portion of the recognition component 450 and the second portion of the recognition component 450 on the biosensor 400.

Figure 9A:
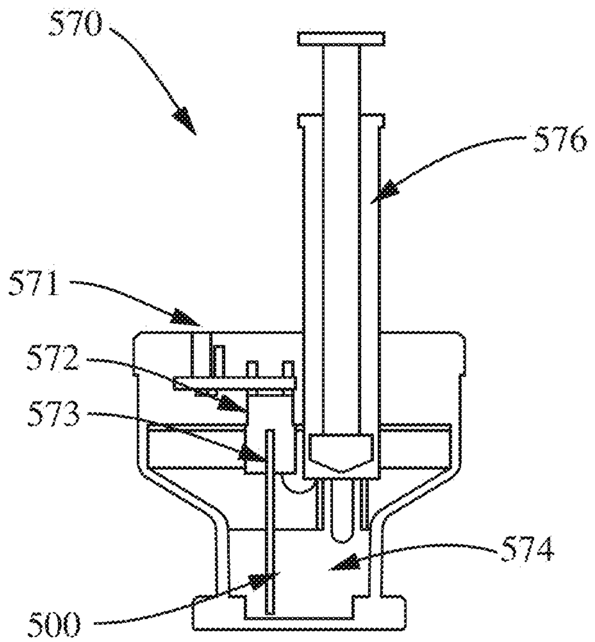
FIGS. 9A and 9B are a cross-sectional and a perspective view of a sample processing unit coupled to an electrochemical biosensor, according to an embodiment.
Figure 9B:
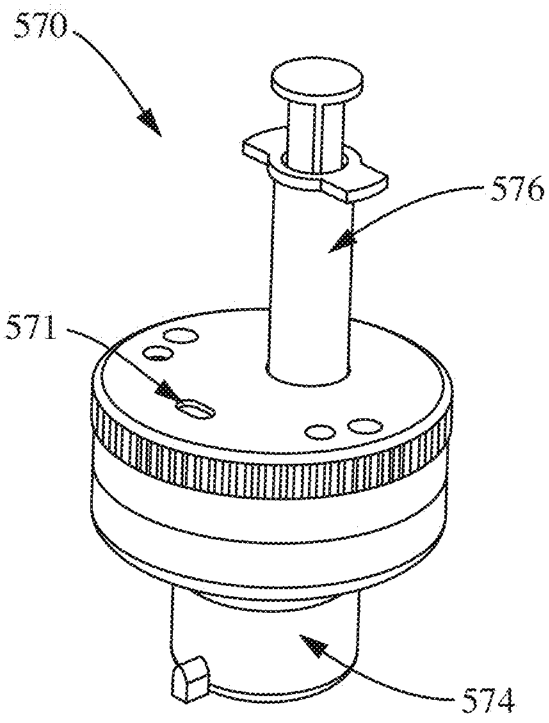
Figure 10:
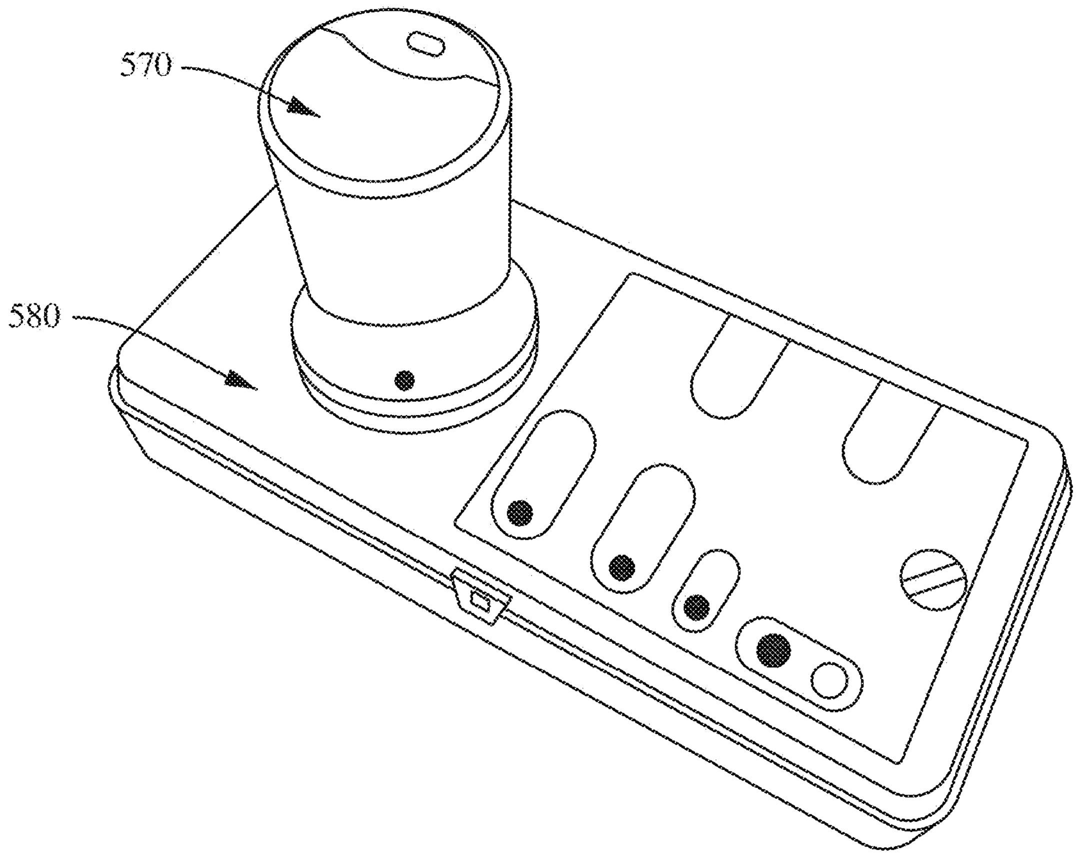
FIG. 10 is a black and white photograph displaying a perspective view of the sample processing unit of FIGS. 9A and 9B coupled to an electrochemical testing unit according to an embodiment.

FIGS. 9A, 9B and 10 show a cross-sectional view and a perspective view of a system comprising a sample processing unit 570, an electrochemical biosensor 500, and an electrochemical testing unit 580, according to an embodiment. The sample processing unit 570 can have a three-dimensional shape comprising a first portion having a length and first circular cross-sectional, and a second portion having a length and second circular cross-sectional. The first portion of the sample processing unit 570 and the second portion of the sample processing unit 570 are coupled and/or connected by a conical section, as shown in FIG. 9A. The sample processing unit 570 is a receptacle that defines an interior volume, compartment, and/or chamber 574 in which biological samples can be received, housed, and/or stored prior to, during and/or after their electrochemical analysis with the biosensor 500. In some embodiments, the sample processing unit 570 can include multiple portions that can be coupled and/or assembled together to form the interior volumes, compartment, and/or chamber 574 for receiving biological samples. That is, in some embodiments, the sample processing unit 570 can be modular. Alternatively, in other embodiments, the sample processing unit 570 can be made of a monolithic structure.

The sample processing unit 570 can be configured to be coupled to one or more external components to facilitate transferring biological samples from the external component to a receptacle of the sample processing unit 570. For example, in some embodiments the sample processing unit 570 can include a receptacle configured receive and couple a syringe 576 containing a biological sample, and a luer lock (not shown) configured to be fluidically coupled to the syringe 576 to allow a user to transfer at least a portion of a biological sample from the syringe 576 to the interior volume, compartment, and/or chamber 574 of the sample processing unit 570 by actuating the plunger of the syringe 576. In some embodiments, the sample processing unit 570 can further include a filtration membrane (not shown) fluidically coupled to the syringe 576 such that the user can actuate the plunger of the syringe 576 to cause a biological sample stored in the syringe 576 to flow from the syringe 576 through the filtration membrane (not shown) and into the interior volume, compartment, and/or chamber 574 of the sample processing unit 570, effectively removing particles and/or other undesired components present in the biological sample. Moreover, in some embodiments the syringe 576 can also provide a fluidic pressure to the interior volume, compartment, and/or chamber 574 of the sample processing unit 570, ensuring an intimate contact between the biological sample the biosensor 500 during the electrochemical analysis of the biological sample.

The sample processing unit 570 can include a cartridge 572 configured to receive the biosensor 500 and expose at least a portion of the biosensor 500 to biological samples stored in the interior volume, compartment, and/or chamber 574 of the sample processing unit 570. The cartridge 572 can be further configured to electrically couple the biosensor 500 to the electrochemical testing unit 580 to conduct electrochemical analysis of the biological samples stored on the sample processing unit 570. The cartridge 572 can include any suitable structure configured to removably receive, secure and/or mechanically immobilize the biosensor 500 to the cartridge 572. For example, as shown in FIG. 9B, the cartridge 572 can include an engineering fit, interreference fit, press fit and/or friction fit 573 configured to receive and immobilize at least a portion of the biosensor 500. That is, the cartridge 572 can include an opening, cavity, slot or the like defining the interference fit 573 configured to secure a first portion of the biosensor 500 by friction.

The cartridge 572 can also be configured to couple the biosensor 500 to the electrochemical testing unit 580 to send and receive electrical signals between the electrochemical testing unit 580 and an electrode (not shown) of the biosensor 500. The cartridge 572 can include a first electrically conductive surface and/or terminal configured to receive a similarly shaped electrically conductive surface and/or terminal of the biosensor 500 (not shown) to establish electrical contact (e.g., continuity). The cartridge 572 can also include a second electrically conductive surface and/or terminal that can be electrically coupled to the electrochemical testing unit 580, such that the electrochemical testing unit 580 and the biosensor 500 can be in electrical contact (e.g., continuity). For example, in some embodiments, the electrically conductive surface and/or terminal can be disposed within an opening, aperture, and/or slot of the cartridge 572 to receive a portion of the biosensor 500 comprising a similar and/or complementary electrically conductive surface and/or terminal. In some embodiments, the electrically conductive surface and/or terminal of the cartridge 572 can include a spring-loaded mechanism configured to exert a force against the biosensor 500 to ensure continuous electrical contact and continuity between the electrode of the biosensor 500 and the sample processing unit 570. Similarly, the cartridge 572 can include a second electrically conductive surface and/or terminal electrically coupled to the electrochemical testing unit 580, such that the electrochemical testing unit 580 and the cartridge 572 are in electrical contact (e.g., continuity).

The electrochemical testing unit 580 can be any suitable electrochemistry workstation capable of generating electrical signals to conduct potentiostat or galvanostat electrochemical characterization techniques and/or diagnostic tests such as cyclic voltammetry (CV), differential pulse voltammetry (DPV), square wave voltammetry, galvanostatic cycling (GC), galvanostatic or potentiostat intermittent titration techniques (GITT or PITT), and/or impedance spectroscopy (EIS). In some embodiments, the electrochemical testing unit 580 can incorporate software programing and/or algorithms configured to conduct predetermined tests and store a library of electrochemical response (e.g., signatures) associated with different biological samples and/or target molecules, facilitating the identification and monitoring the composition of biological samples of interest.

In some embodiments, the sample processing unit 570 and/or the cartridge 572 can include an electromagnetic shield configured to block electromagnetic radiation and radio frequencies (e.g., an RF shield) reducing the interference caused by light pollution (e.g., infrared, visible, and/or UV light produced by multiple sources including sun light, Light Emitting Diodes (LEDs), Halogen lamps, Xenon lamps, incandescent lamps, and the like; radio waves, electromagnetic fields, and/or electrostatic fields generated by external sources such a wireless fidelity (WI FI) network, mobile phones, short-range wireless communication devices (Bluetooth), and consumer electronic devices. The RF shield can include a field barrier made of conductive or magnetic materials that isolate the biosensor 500 from its surroundings, preventing evolution of noisy electrical signals during electrochemical analysis of a biological samples caused by external factors. The RF shield can be any suitable size and shape. In some embodiments, the RF shield can an enclosure made of one or more metals such as Aluminum, copper, brass, nickel, silver, steel, and tin that act as a Faraday cage. In some embodiments, the RF shield can be made of sheet metal, metal screen, and/or a metal foam. In some embodiments, the RF shield can include a plastic enclosure coated on the inside with a metallic ink consisting of a carrier material loaded with a suitable metal, typically Aluminum, copper or nickel, in the form of very small particulates.

In some embodiments, the sample processing unit 570 and/or the electrochemical testing unit 580 can be coupled to an external device via a port 571 which can be used to and/or otherwise configured to monitor and control the sample processing unit 570 and/or the electrochemical testing unit 580. In some embodiments, the external device can be configured to monitor and/or control the sample processing unit and/or the electrochemical testing unit via a control algorithm, an artificial intelligence algorithm, a machine learning algorithm or system, a human operator, and/or any suitable combination thereof. For example, in some instances, a user can provide an operational command to the sample processing unit 570 and/or the electrochemical testing unit 580 via a user interface by sending a signal via the external device, which can be a personal computer, a workstation, a mobile device, a tablet, a wearable electronic device, and/or any other suitable compute device. The signal can be indicative of the operational command to the sample processing unit 570 and/or the electrochemical testing unit 580.

Figure 11A:
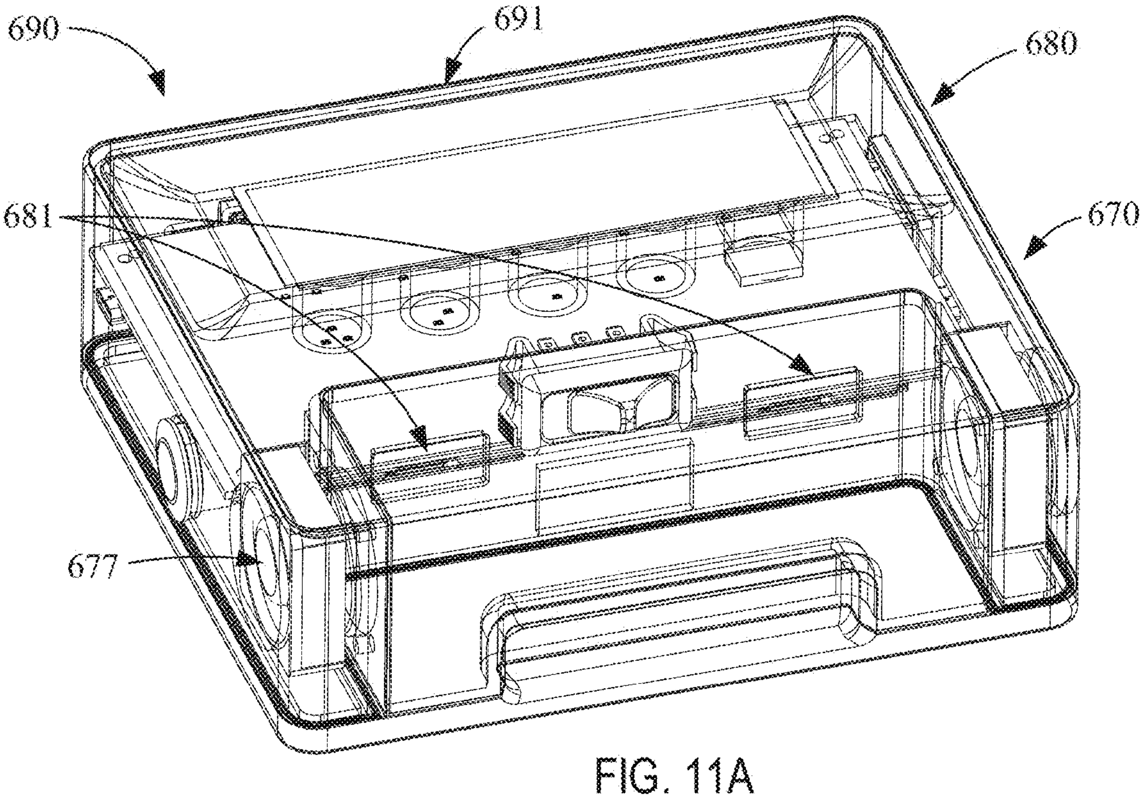
FIGS. 11A and 11B are perspective views of a system that integrates a sample processing unit, and an electrochemical testing unit for the electrochemical analysis of biological samples comprising one or more target species, and according to an embodiment.
Figure 11B:
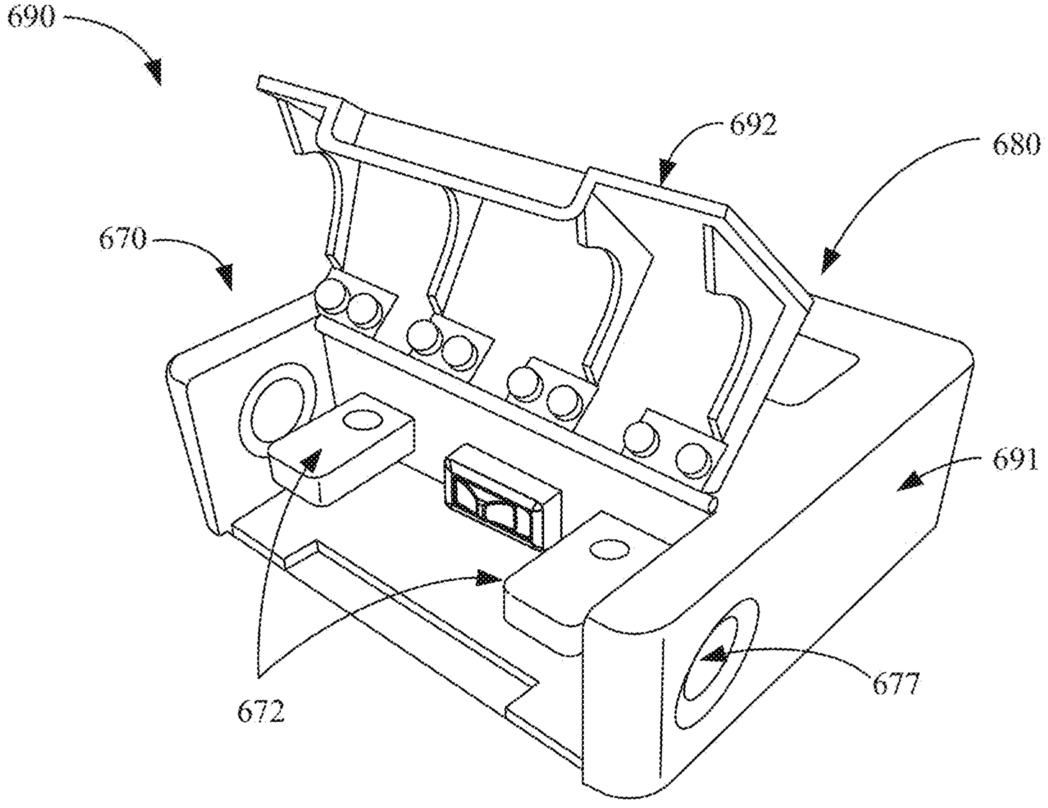

FIGS. 11A and 11B show a perspective view of a system 690 that integrates a sample processing unit 670, and an electrochemical testing unit 680, and according to an embodiment. The system 690 can include a housing 691 that defines one or more interior volumes in which the components of the sample processing unit 670 and the electrochemical testing unit 680 can be accommodated and/or housed. In some embodiments, the housing 691 can resemble and/or be a rectangular parallelepiped shape, as shown in FIGS. 11A and 11B. The housing 691 can be have any suitable size and/or dimensions configured to accommodate the components of the sample processing unit 670 and the electrochemical testing unit 680. In some embodiments, the housing 691 can include multiple portions that can be coupled and/or assembled together to form one or more interior volumes, compartments, and/or chambers for receiving the components of the sample processing unit 670 and the electrochemical testing unit 680. That is, in some embodiments, the housing 691 can be modular. Alternatively, in other embodiments, the housing 691 can be made of a monolithic structure.

The housing 691 can define a first portion and/or volume in which the sample processing unit 670 can be accommodated and/or housed. Similarly, housing 691 can define a second portion and/or volume in which the electrochemical testing unit 680 can be accommodated and/or housed. The first portion and/or volume of the housing 691 can include a set of walls that enclose and provide support to dispose and/or accommodate the components of the sample processing unit 670. For example, as shown in FIG. 11B, the housing 691 includes a set of walls that enclose an interior chamber and/or volume of the sample processing unit 670 in which two cartridges 672 can be removably disposed and/or accommodated. The set of walls can also be used to accommodate and/or provide support to one or more fans 677. The fans 677 can be any suitable fan configured to cool the interior interior chamber and/or volume of the sample processing unit 670 and/or to maintain a controlled temperature on the interior chamber and/or volume of the sample processing unit 670.

The system 690 can also include a lid 692 disposed on a front side of the housing 691, as shown in FIG. 11B. The lid 692 can be operated manually and/or automatically (via a control unit of the system 690) to open and/or close and grant access to the interior volume or chamber of the sample processing unit 670. With the lid 692 opened, the cartridges 672 can be disposed in the sample processing unit 670 and be electrically coupled to the electrochemical testing unit 680, as further described herein. In some embodiments, the set of walls of the sample processing unit 670 and the lid 692 can collectively form an electromagnetic shield configured to block electromagnetic radiation and prevent interference of the electromagnetic radiation with the biosensors described herein. The electromagnetic shield (e.g., an RF shield) can block electromagnetic radiation and radio frequencies caused by light pollution (e.g., infrared, visible, and/or UV light produced by multiple sources including sun light, Light Emitting Diodes (LEDs), Halogen lamps, Xenon lamps, incandescent lamps, and the like; radio waves, electromagnetic fields, and/or electrostatic fields generated by external sources such a wireless fidelity (WI FI) network, mobile phones, short-range wireless communication devices (Bluetooth), and consumer electronic devices. The RF shield can include a field barrier made by applying and/or disposing a coating material on the set of walls and the lid 692. The coating material can include conductive or magnetic materials that isolate the biosensors from its surroundings, preventing evolution of noisy electrical signals during electrochemical analysis of a biological samples caused by external factors. In some embodiments, the RF shield can be made of one or more metals such as Aluminum, copper, brass, nickel, silver, steel, and tin that act as a Faraday cage. For example, in some embodiments, the RF shield can be made by coating a metallic ink consisting of a carrier material loaded with suitable metals, typically Aluminum, copper or nickel, in the form of very small particulates. In other embodiments, the RF shield can be made of sheet metal, metal screens, and/or a metal foam disposed on the set of walls and the interior, (and/or on the exterior) of the lid 692.

FIG. 11B show the housing 691 includes a rear portion in which all the electrical components, electric circuits, and auxiliary accessories (not shown) of the electrochemical testing unit 680 can be accommodated and/or housed. The electrochemical testing unit 680 can be any suitable electrochemistry workstation capable of generating electrical signals to conduct potentiostat or galvanostat electrochemical characterization techniques and/or diagnostic tests. The electrochemical testing unit 680 can be similar to and/or substantially the same as one or more portions (and/or combination of portions) of the electrochemical testing unit 180, and 580 described above. Consequently, portions and/or components of the electrochemical testing unit 680 may not be described in further detail herein.

Figure 11C:
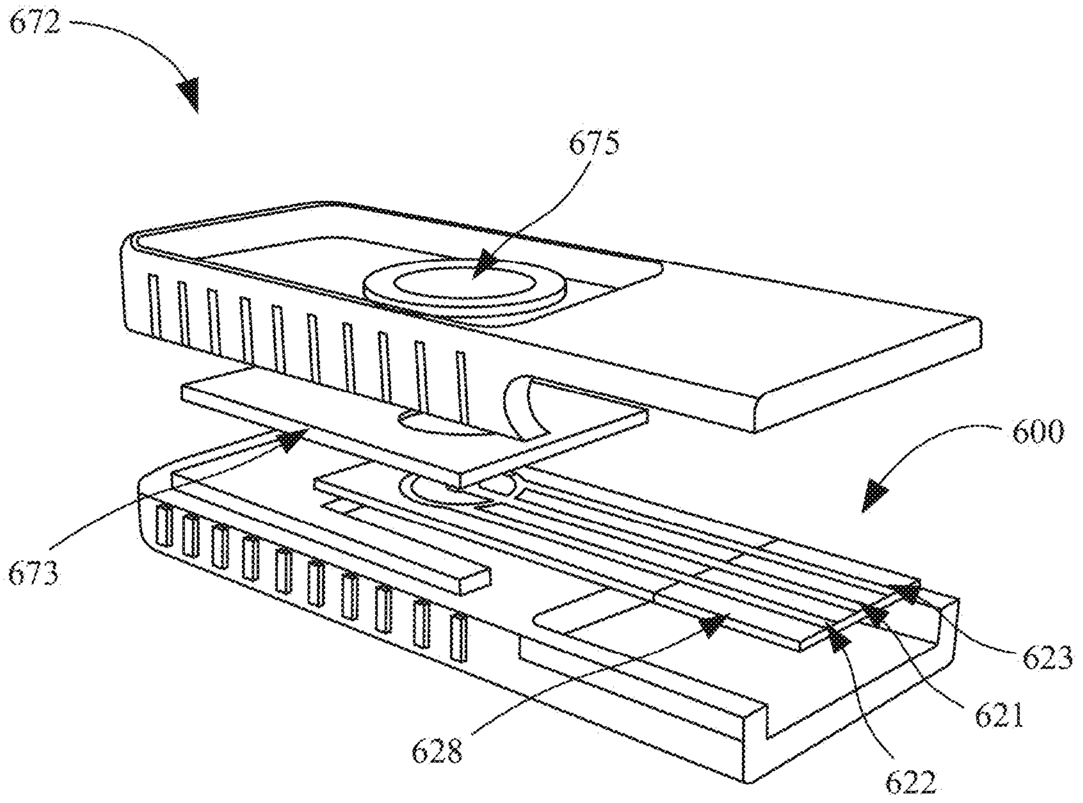
FIG. 11C is a partially exploded perspective view of a cartridge that can be coupled to a biosensor and to the system shown in FIGS. 11A and 11B, for the electrochemical analysis of biological samples comprising one or more target species, and according to an embodiment.

FIG. 11C shows a partially exploded perspective view of a cartridge 672, according to an embodiment. The cartridge 672 can be similar to and/or substantially the same as one or more portions (and/or combination of portions) of the cartridges 172 and 572 described above. Consequently, portions and/or components of the cartridge 672 may not be described in further detail herein. The cartridge 672 can be configured to receive a biosensor 600 and expose at least a portion of the biosensor 600 to biological samples. The biosensor 600 can be similar and/or the same as the biosensor 100, 200, 300, 400, and/or 500 described above. For example, the biosensor 600 can include a standard screen-printed electrode strip comprising a working electrode 621, a counter electrode 622, and a reference electrode 623 disposed on a plastic and/or ceramic support 628. In some embodiments, the working electrode 621, the counter electrode 622, and the reference electrode 623 can be made of any suitable material including gold (Au), platinum (Pt), silver (Ag), carbon (C), carbon nanotubes (CNT), and the like.

The cartridge 672 can also include any suitable structure configured to removably receive, secure and/or mechanically immobilize the biosensor 600 to the cartridge 672. For example, as shown in FIG. 11C, the cartridge 572 can include an engineering fit, interreference fit, press fit and/or friction fit 673 configured to receive and immobilize at least a portion of the biosensor 500. That is, the interference fit 673 can be configured to secure a portion of the biosensor 600 by friction. The cartridge 672 can also include an opening, cavity, and/slot 675 which can be used to receive a biological sample for analysis. The opening 675 provides and/or defines a reservoir that can accommodate a volume of a biological sample. In some embodiments, the volume of the reservoir defined by the opening 675 can be about 1 μL, about 2 μL, about 5 μL, about 10 μL, about 20 μL, about 50 μL, about 100 μL, about 200 μL, about 500 μL, about 1 mL, about 2 mL, about 2 mL, about 5 mL, about 10 mL, about 20 m, about 30 mL, about 40 mL, or about 50 mL, inclusive of all values and ranges therebetween. The cartridge 672 can also be configured to couple the biosensor 600 to the electrochemical testing unit 680 to send and receive electrical signals between the electrochemical testing unit 680 and an electrode of the biosensor 600. In some embodiments, the cartridge 672 can include multiple portions that can be coupled and/or assembled together for receiving biological samples, as shown in FIG. 11C. That is, in some embodiments, the cartridge 672 can be modular. Alternatively, in other embodiments, the cartridge 672 can be made of a monolithic structure.

FIGS. 11A and 11B show that two cartridges 672 can be disposed inside the sample processing unit 670 when the lid 692 is open. More specifically, each one of the cartridges 672 can be coupled to a port 681 of the electrochemical testing unit 680. The ports 681 can be disposed on a surface of the electrochemical testing unit 680 adjacent to the interior volume of the sample processing unit 670 defined by the set of walls of the housing 691 and the lid 692 described above. The ports 681 can include one or more electrically conductive surfaces and/or terminals configured to receive similarly shaped electrically conductive surfaces and/or terminals of the biosensor 600 (e.g., the working electrode 621, the counter electrode 622, and/or the reference electrode 623, not shown in FIGS. 11*a* and 11B) to establish electrical contact (e.g., continuity). In some embodiments, the electrically conductive surface and/or terminal of the ports 681 can include a spring-loaded mechanism (not shown) configured to exert a force against the biosensor 600 to ensure continuous electrical contact and continuity between the electrode of the biosensor 600 and the sample processing unit 670.

In use, one or more biological samples can be disposed on the cartridges 672 for conducting their electrochemical analysis. The biological samples can be collected and transferred (via a pipette) to the reservoir defined by the opening 675 of the cartridge 672. The biological samples can be saliva samples, urine samples, blood samples, plasma samples, serum samples, or the like. The biological samples can comprise a target species such as an antigen, toxin, and/or other foreign substance associated with fungi, parasites, pathogenic bacteria and/or viruses, which can be selectively bound and/or conjugated by a recognition component of the biosensor 600. In some instances, the biological sample can be mixed with a volume of a reporter molecule to produce a biological sample mixture. The volume of the reporter molecule added can be adjusted such that the biological sample mixture includes a predetermined concentration of the reporter molecule. The biological sample mixture can be then pipetted to the reservoir defined by the opening 675 of the cartridge 672. In other instances, a volume of a biological sample can be pipetted directly on the reservoir defined by the opening 675 of the cartridge 672. Subsequently, a volume of the reporter molecule at a predetermined concentration can be added to the reservoir defined by the opening 675 of the cartridge 672. The biological sample and the reporter molecule can then be allowed to mix on the reservoir defined by the opening 675, forming a biological sample mixture.

The cartridges 672 with the biological samples loaded and/or disposed on the reservoirs defined by the openings 675 can be introduced on the sample processing unit 670 when the lid 692 is opened (either automatically, by the system 690, or manually, by a user and/or technician). The cartridges 672 can be coupled to the electrochemical testing unit 680 via the ports 681, such that the electrodes 631, 632, and 630 of the biosensor 600 are electrically coupled to the electrochemical testing unit 600. Electrical signals such as DPV can be generated by the electrochemical testing unit 680 and sent and/or applied to the working electrode 621 to initiate the electrochemical analysis of the biological sample comprising the target species and determine the presence and/or the concentration of the target species, as described above.

Figure 12:
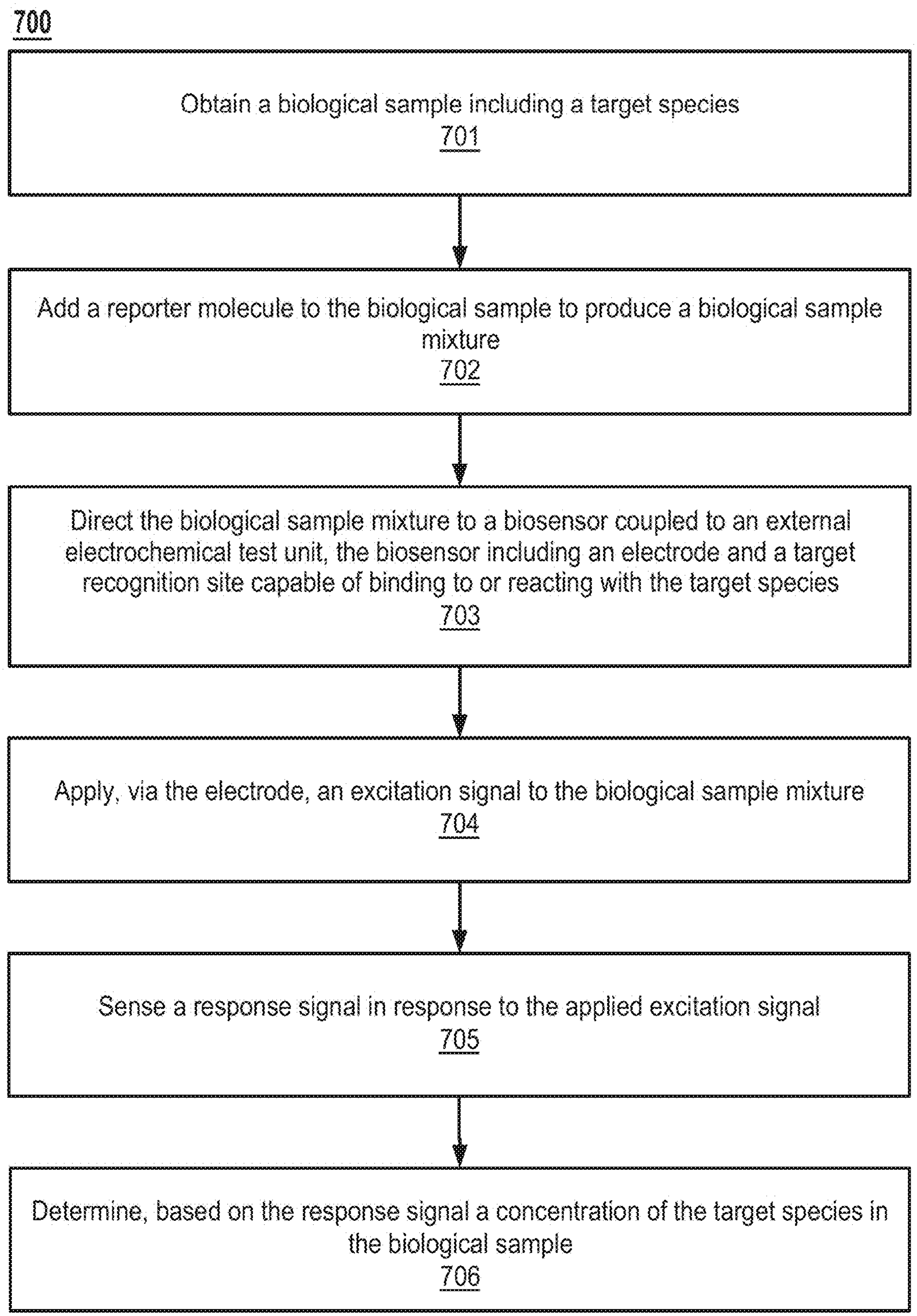
FIG. 12 is a flow chart of an example method of using an electrochemical biosensor to determine a concentration of a target species in a biological sample, according to an embodiment.

FIG. 12 shows flow chart of an example method 700 of using an electrochemical biosensor to determine a concentration of a target species in a biological sample such as those described herein. In some embodiments, the biosensor can be similar to and/or substantially the same as any of the biosensor 100, 200, 300, 400, 500 and/or 600 working with any of the sample processing units and electrochemical testing units described herein.

The method 700 includes obtaining a biological sample including a target species at step 701. The biological sample can be received and/or disposed on an interior volume, compartment, and/or chamber of a sample processing unit. For example, in some instances, a user and/or technician can dispose the biological sample on the interior volume, compartment, and/or chamber of the sample processing unit by collecting the biological sample in a syringe, coupling the syringe with the biological sample inside the syringe on a receptacle of the sample processing unit configured to couple fluidically the syringe with the interior volume, compartment, and/or chamber of the sample processing unit, and actuating the plunger of the syringe to cause the biological sample stored in the syringe to flow from the syringe into the interior volume, compartment, and/or chamber of the sample processing unit. In other embodiments, a user and/or technician can dispose a biological sample on an interior volume, compartment, and/or chamber of the sample processing unit by collecting the biological sample with a pipette. The biological sample contained inside a pipette tip, can then be disposed on a reservoir included on a cartridge. The cartridge can then be coupled to an interior volume, compartment, and/or chamber of the sample processing unit.

The method 700 includes adding a reporter molecule to the biological sample to produce a biological sample mixture, at step 700. In some instances, for example, the biological sample can be mixed with a solution containing the reporter molecule by disposing the biological sample within an interior volume, compartment, and/or chamber of the sample preparation unit, disposing a volume of the solution containing the reporter molecule in a separate interior volume, compartment, and/or chamber of the sample preparation unit, and transporting a flow of the solution containing the reporter molecule through microfluid channels that communicate fluidically the interior volume, compartment, and/or chamber comprising the solution containing the reporter molecule and the interior volume, compartment, and/or chamber comprising the biological sample, producing a biological sample mixture that has a predetermined concentration of reporter molecule. In some instances, the biological sample can be mixed with the solution containing the reporter molecule (to produce a biological sample mixture) by disposing a volume of the solution containing the reporter molecule with a pipette, a syringe, and/or the like, into an interior volume, compartment, and/or chamber of the sample processing unit that stores and/or contains the biological sample. In some instances, the biological sample can be mixed with the solution containing the reporter molecule (to produce a biological sample mixture) by disposing a volume of the solution containing the reporter molecule with a pipette, a syringe, and/or the like, into a reservoir of a cartridge which also stores and/or contains the biological sample.

The method 700 includes, at step 703, contacting the biological sample mixture with a biosensor coupled to an electrochemical testing unit, the biosensor including an electrode and a target recognition site capable of binding to or reacting with the target species. In some instances, a user can couple a syringe containing the biological sample to a receptacle of the sample preparation unit; and actuate the plunger of the syringe to cause a biological sample stored in the syringe to flow from the syringe into an interior volume, compartment, and/or chamber of the sample processing unit in which the at least a portion of the biosensor is disposed on. Moreover, in some instances, the user can actuate the plunger of the syringe to provide a fluidic pressure to the interior volume, compartment, and/or chamber of the sample processing unit to ensure an intimate contact between the biological sample the biosensor during the electrochemical analysis of the biological sample. In some instances, as described above, the biological sample mixture can be disposed on reservoir of a cartridge. The cartridge can be coupled to a biosensor such that the reservoir facilitates fluidically coupling the biological sample mixture with the biosensor. In such embodiments, the cartridge can be coupled to a port of an electrochemical testing unit.

The method 700 includes, at step 704, applying, via the electrode, an excitation signal to the biological sample mixture. In some instances, the excitation signals can be generated by the electrochemical testing unit and sent and/or applied to the biosensor electrically coupled to the electrochemical testing unit. In some instances, for example, the excitation signal can be selected from a variety of voltammetric method such as a linear sweep, cyclic voltammetry, pulse voltammetry, DPV, square wave voltammetry, stripping voltammetry or the like. For example, in some instances the excitation signals generated by the electrochemical testing unit and sent and/or applied to biosensor during the electrothermal analysis of a biological sample can include a DPV signal. During the DPV analysis, a series of regular voltage pulses are superimposed on a linearly increased potential sweep. Current is measured immediately before each voltage pulse and at the end of the pulse, and the difference between them is recorded as a function of the potential.

At step 705, the method 700 includes sensing a response signal in response to the applied excitation signal. In some instances, for example, the excitation signal can initiate a reversible electrochemical reaction of the reporter molecule, causing the reporter molecule to electrostatically bind with the species present in the biological sample including a target species, proteins, antigens, toxins, and/or other analytes, and induce a response signal consisting of an electrical current on the biosensor which can be detected, measured and monitored with the electrochemical testing unit.

At step 706, the method 700 includes determining, based on the response signal a concentration of the target species in the biological sample. The response signal includes an electrical current that is inversely proportional to the concentration of the target species present on the biological sample. In some instances, determining the concentration of the target species in the biological sample includes comparing the response signal with a control response signal measured by the biosensor with a control sample. For example, control samples can be obtained from individuals which do not carry and/or have a pathogen associated with the target species, and thus samples obtained from such individuals do not include the target species. The control samples can be mixed with the solution containing the reporter molecule to produce a control sample mixture which has the predetermined concentration of reporter molecule. The control sample mixtures can be measured with the biosensor as described above with respect to the biological samples to generate a control response signal. The control response signal includes a control electrical current which can be compared with the electrical current measured with the biological sample. Biological samples that do include the target species generate an electrical current that is smaller than the control electrical current, with the difference between the electrical current and the control electrical current being proportional to the concentration of target species present in the biological sample. In some instances, the response signal includes DPVs in which the current measured is inversely proportional to the concentration of target species. In some instances, the DPV responses obtained during electrochemical analysis of biological samples with the biosensor can be used to create a standard curve, which can be validated with for example, other analytical methods such as ELISA.

While various embodiments have been described above, it should be understood that they have been presented by way of example only, and not limitation. While the embodiments have been particularly shown and described, it will be understood that various changes in form and details may be made. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above. For example, as described above, the biosensor 300 can be a combination of certain features and/or aspects of the biosensor 100 and the biosensor 200

The invention claimed is:

1. A method, comprising:

contacting a first solution comprising an anchor layer with an electrode for a first period of time, the anchor layer including a first chemical functionality and a second chemical functionality, the first chemical functionality being configured to immobilize the anchor layer to the electrode, wherein the second chemical functionality comprises a carboxylic acid functional group;

contacting a second solution comprising a site-blocking reagent with the electrode for a second period of time;

contacting a third solution comprising a linker with the electrode for a third period of time, the linker being configured to bind to the second chemical functionality of the anchor layer; and contacting a fourth solution comprising a recognition component with the electrode for a fifth period of time, while a first electrical signal including at least one of a differential pulse voltammetry signal or a square wave voltammetry signal is applied to the electrode, wherein the method is used to fabricate a biosensor, the biosensor including:

the electrode configured to receive a second electrical signal;

the anchor layer disposed on the electrode and including the first chemical functionality and the second chemical functionality;

the linker covalently bound to the second chemical functionality of the anchor layer; and the recognition component conjugated to the linker and disposed at an orientation with respect to the electrode, wherein the orientation of the recognition component comprises a tail-on orientation with respect to the electrode, the recognition component being configured to selectively bind a target species when the second electrical signal is received by the electrode.

2. The method of claim 1, wherein the site-blocking reagent is 6-Mercapto-1 Hexanol.

3. The method of claim 1, further comprising flowing a gas stream over the electrode for a fourth period of time prior to the step of contacting the second solution.

4. The method of claim 3, wherein the fourth period of time is about 30 to 90 minutes.

5. The method of claim 1, wherein the first electrical signal is applied to the electrode for a period of time of about 20 to 40 seconds.

6. The method of claim 1, wherein the electrode comprises at least one of a gold, carbon, or graphene electrode.

7. The method of claim 1, wherein the first chemical functionality comprises a sulfur-containing group selected from a thiol, a disulfide, or a sulfide group.

8. The method of claim 1, wherein the linker comprises a primary amine group.

9. The method of claim 1, wherein the linker comprises a biotin-binding protein.

10. The method of claim 9, wherein the biotin-binding protein comprises streptavidin.

11. The method of claim 1, wherein the recognition component comprises an antibody, an aptamer, or an affinity molecule.

12. The method of claim 11, wherein the recognition component comprises the antibody and the antibody is a biotinylated antibody.

13. The method of claim 1, further comprising etching at least a portion of the electrode prior to contacting the electrode with the first solution.

14. The method of claim 13, wherein the etching comprises exposing the electrode to an etching solution.

15. The method of claim 14, wherein the etching solution comprises potassium iodide or iodine.

16. The method of claim 1, wherein the site-blocking reagent comprises a linear hydrocarbon having chirality and a thiol functional group disposed at a first end of the site-blocking reagent and a hydroxyl group bound to a second end of the site-blocking reagent.

17. The method of claim 1, wherein the linker is covalently bound to the second chemical functionality of the anchor layer by exposing the second chemical functionality and the linker to a carbodiimide additive.

18. The method of claim 17, wherein the carbodiimide additive comprises 1-Ethyl-3-(3-dimethylaminopropyl) carbodiimide (EDC), N-hydroxysuccinimide (NHS), or a water-soluble sulfonated analogue of NHS.

* * * * *